US008357666B2

(12) United States Patent
Eilertsen et al.

(10) Patent No.: US 8,357,666 B2
(45) Date of Patent: Jan. 22, 2013

(54) REPROGRAMMING A CELL BY INDUCING A PLURIPOTENT GENE THROUGH RNA INTERFERENCE

(75) Inventors: Kenneth J. Eilertsen, Baton Rouge, LA (US); Rachel A. Power, Zachary, LA (US); Jong S. Rim, Baton Rouge, LA (US)

(73) Assignee: Nupotential, Inc., Baton Rouge, LA (US)

( * ) Notice: Subject to any disclaimer, the term of this patent is extended or adjusted under 35 U.S.C. 154(b) by 189 days.

(21) Appl. No.: 12/384,667

(22) Filed: Apr. 7, 2009

(65) Prior Publication Data
US 2009/0269763 A1 Oct. 29, 2009

Related U.S. Application Data

(63) Continuation-in-part of application No. 11/497,064, filed on Aug. 1, 2006, now Pat. No. 7,601,699.

(60) Provisional application No. 60/704,465, filed on Aug. 1, 2005, provisional application No. 61/043,066, filed on Apr. 7, 2008, provisional application No. 61/042,890, filed on Apr. 7, 2008, provisional application No. 61/042,995, filed on Apr. 7, 2008, provisional application No. 61/113,971, filed on Nov. 12, 2008.

(51) Int. Cl.
*A61K 48/00* (2006.01)
*C07H 21/02* (2006.01)
*C07H 21/04* (2006.01)
*C12N 15/85* (2006.01)
*C12Q 1/70* (2006.01)

(52) U.S. Cl. ............ 514/44; 536/23.1; 536/24.5; 435/6; 435/325

(58) Field of Classification Search ........................ None
See application file for complete search history.

(56) References Cited

U.S. PATENT DOCUMENTS

| | | | |
|---|---|---|---|
| 4,352,883 | A | 10/1982 | Lim |
| 4,353,888 | A | 10/1982 | Sefton |
| 4,968,733 | A | 11/1990 | Muller et al. |
| 4,976,859 | A | 12/1990 | Wechs |
| 5,082,670 | A | 1/1992 | Gage et al. |
| 5,084,350 | A | 1/1992 | Chang et al. |
| 5,158,881 | A | 10/1992 | Aebischer et al. |
| 5,284,761 | A | 2/1994 | Aebischer et al. |
| 5,618,531 | A | 4/1997 | Cherksey |
| 6,498,018 | B1 | 12/2002 | Carpenter |
| 2005/0084968 | A1 | 4/2005 | Nakatsuji et al. |
| 2005/0170506 | A1 | 8/2005 | Sayre et al. |
| 2007/0032447 | A1 | 2/2007 | Eilertsen |
| 2008/0066197 | A1 | 3/2008 | Ying et al. |

FOREIGN PATENT DOCUMENTS

| | | |
|---|---|---|
| WO | 9219195 | 11/1992 |
| WO | 9505452 | 2/1995 |
| WO | 02051980 A2 | 7/2002 |

OTHER PUBLICATIONS

Leu et al., Double RNA Interference of DNMT3B and DNMT1 Enhances DNA Demethylation and Gene Reactivation, 2003, Cancer Research, 63, pp. 6110-6115.*
Written Opinion and International Search Report mailed Nov. 24, 2009 for PCT App. No. PCT/US09/039815 filed on Apr. 7, 2009.
Park, I., "Reprogramming of human somatic cells to pluripotency with defined factors", Nature Articales, vol. 451/10, pp. 141-147, Jan. 2008.
Eilertsen, K.J., "Targeting cellular memory to reprogram the epigenome, restore potential, and improve somatic cell nuclear transfer", Animal Reproduction Science 98 129-146, 2007.
Written Opinion and International Search Report mailed Dec. 2, 2009 for PCT App. No. PCT/US2009/002161 filed on Apr. 7, 2009.
Wegmuller, D., "A cassette system to study embryonic stem cell differentiation by inducible RNA interference", Stemm Cells, 25, 1178-1185, 2007.
Singh, S.K., "REST maintains self-renewal and pluripotency of embryonic stem cells", Nature Letters, vol. 453, 223-229, May 8, 2008.
Pan, G., "A negative feedback loop of transcription factors that controls stem cell pluripotency and self-renewal", FASEB Journal, vol. 20, pp. E1094-E1102, 2006.
Fong, H., "Regulation of self-renewal and pluripotency by Sox2 in human embryonic stem cells", Stem Cells, 26, 1931-1938, 2008.
Karantzali, E., "Histone deacetylase inhibition accelerates the early events of stem cell differentiation: transcriptomic and epigenetic analysis", Genome Biology, vol. 9, Issue 4, Article R65, Apr. 4, 2008.
Written Opinion and International Search Report mailed Dec. 2, 2009 for PCT App. No. PCT/US2009/002163 filed on Apr. 7, 2009.
McCool, K.W., "The role of histone acetylation in regulating early gene expression patterns during early embryonic stem cell differentiation", Journal of Biological Chemistry, vol. 282, No. 9, 6696-6706, Mar. 2, 2007.

(Continued)

*Primary Examiner* — Amy Bowman
(74) *Attorney, Agent, or Firm* — Whyte Hirschboeck Dudek S.C.; Michael J. Cronin

(57) ABSTRACT

The invention relate to methods, compositions, and kits for reprogramming a cell. In one embodiment, the invention relates to a method for inducing the expression of at least one gene that contributes to a cell being pluripotent or multipotent. In yet another embodiment, the method comprises inhibiting the expression of a gene that codes for a protein involved in transcriptional repression. In yet another embodiment, the invention relates to a reprogrammed cell or an enriched population of reprogrammed cells that can have characteristics of an ES-like cell, which can be re- or trans-differentiated into a differentiated cell type.

6 Claims, 8 Drawing Sheets

OTHER PUBLICATIONS

Gan, Q., "Concise review; Epigenetic mechanisms contribute to pluripotency and cell lineage determination of embryonic stem cells", Stem Cells, vol. 25, 2-9, 2007.

Siebzehnrubl, F.A., "Histone deacetylase inhibitors increase neuronal differentiation in adult forebrain precursor cells", Exp Brain Res, vol. 176, 672-678, 2007.(1 page only).

* cited by examiner

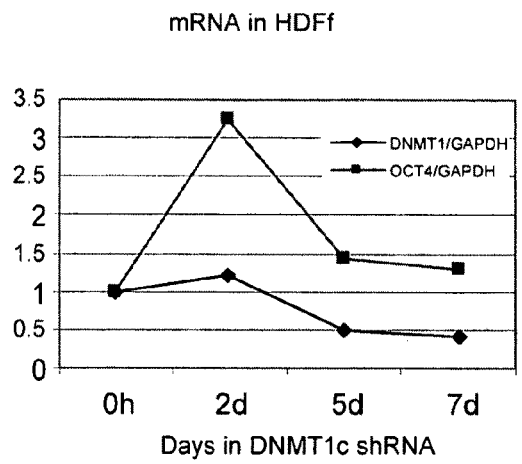 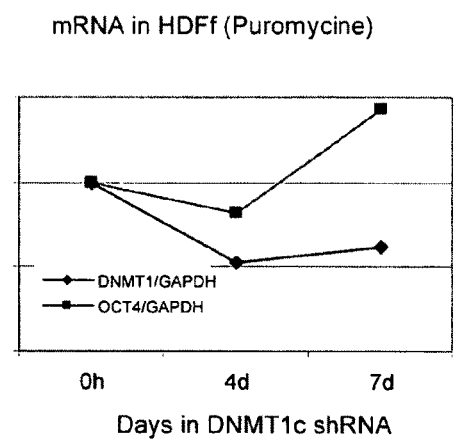
FIG. 3A  FIG. 3B
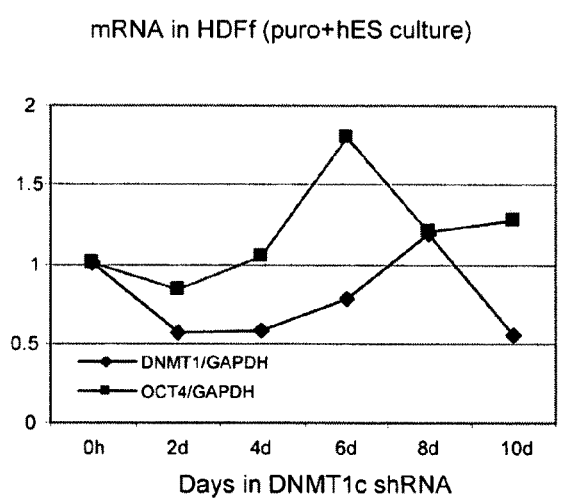
FIG. 3C

SEQUENCE LISTING

<160> NUMBER OF SEQ ID NOS: 4

<210> SEQ ID NO 1
<211> LENGTH: 19
<212> TYPE: DNA
<213> ORGANISM: Homo sapiens

<400> SEQUENCE: 1
gtctaccaga tcttcgata                                                            19

<210> SEQ ID NO 2
<211> LENGTH: 19
<212> TYPE: DNA
<213> ORGANISM: Homo sapiens

<400> SEQUENCE: 2
gctttcagga tagtcgtga                                                            19

<210> SEQ ID NO 3
<211> LENGTH: 19
<212> TYPE: DNA
<213> ORGANISM: Homo sapiens

<400> SEQUENCE: 3
agcgagactt catggacga                                                            19

<210> SEQ ID NO 4
<211> LENGTH: 19
<212> TYPE: DNA
<213> ORGANISM: Homo sapiens

<400> SEQUENCE: 4
tggtggtata caatgcagg                                                            19

REPROGRAMMING A CELL BY INDUCING A PLURIPOTENT GENE THROUGH RNA INTERFERENCE

CROSS-REFERENCE TO RELATED PATENT APPLICATIONS

This application is a continuation-in-part of U.S. patent application Ser. No. 11/497,064, filed Aug. 1, 2006, which claims benefit under 35 U.S.C. §119(e) of U.S. Provisional Application 60/704,465, filed Aug. 1, 2005, and also claims benefit under 35 U.S.C. §119(e) of U.S. Provisional Application 61/042,890, filed Apr. 7, 2008; U.S. Provisional Application 61/043,066, filed Apr. 7, 2008; U.S. Provisional Application 61/042,995, filed on Apr. 7, 2008; and U.S. Provisional Application 61/113,971, filed Nov. 12, 2008, each of which is incorporated herein by reference as if set forth in its entirety.

FIELD OF THE INVENTION

Embodiments of the invention relate to the fields of cell biology, stem cells, cell differentiation, somatic cell nuclear transfer and cell-based therapeutics. More specifically, embodiments of the invention are related to methods, compositions and kits for reprogramming cells and cell-based therapeutics.

BACKGROUND OF THE INVENTION

Regenerative medicine holds great promise as a therapy for many human ailments, but also entails some of the most difficult technical challenges encountered in modern scientific research. The technical challenges to regenerative medicine include low cloning efficiency, a short supply of potentially pluripotent tissues, and a generalized lack of knowledge as to how to control cell differentiation and what types of embryonic stem cells can be used for selected therapies. While ES cells have tremendous plasticity, undifferentiated ES cells can form teratomas (benign tumors) containing a mixture of tissue types. In addition, transplantation of ES cells from one source to another likely would require the administration of drugs to prevent rejection of the new cells.

Attempts have been made to identify new avenues for generating stem cells from tissues that are not of fetal origin. One approach involves the manipulation of autologous adult stem cells. The advantage of using autologous adult stem cells for regenerative medicine lies in the fact that they are derived from and returned to the same patient, and are therefore not subject to immune-mediated rejection. A drawback is that these cells lack the plasticity and pluripotency of ES cells and thus their potential is uncertain. Another approach is aimed at reprogramming somatic cells from adult tissues to create pluripotent ES-like cells. However, this approach has been difficult as each cell type within a multicellular organism has a unique epigenetic signature that is thought to become fixed once cells differentiate or exit from the cell cycle.

Cellular DNA generally exists in the form of chromatin, which is a complex comprising nucleic acid and protein. Indeed, most cellular RNA molecules also exist in the form of nucleoprotein complexes. The nucleoprotein structure of chromatin has been the subject of extensive research, as is known to those of skill in the art. In general, chromosomal DNA is packaged into nucleosomes. A nucleosome comprises a core and a linker. The nucleosome core comprises an octamer of core histones (two each of H2A, H2B, H3 and H4) around which is wrapped approximately 150 base pairs of chromosomal DNA. In addition, a linker DNA segment of approximately 50 base pairs is associated with linker histone H1. Nucleosomes are organized into a higher-order chromatin fiber and chromatin fibers are organized into chromosomes. See, for example, Wolffe "Chromatin: Structure and Function" 3.sup.rd Ed., Academic Press, San Diego, 1998.

Chromatin structure is not static, but is subject to modification by processes collectively known as chromatin remodeling. Chromatin remodeling can serve, for example, to remove nucleosomes from a region of DNA, to move nucleosomes from one region of DNA to another, to change the spacing between nucleosomes or add nucleosomes to a region of DNA in the chromosome. Chromatin remodeling can also result in changes in higher order structure, thereby influencing the balance between transcriptionally active chromatin (open chromatin or euchromatin) and transcriptionally inactive chromatin (closed chromatin or heterochromatin).

Chromosomal proteins are subject to numerous types of chemical modification. One mechanism for the posttranslational modification of these core histones is the reversible acetylation of the .epsilon.-amino groups of conserved highly basic N-terminal lysine residues. The steady state of histone acetylation is established by the dynamic equilibrium between competing histone acetyltransferase(s) and histone deacetylase(s) herein referred to as HDAC. Histone acetylation and deacetylation has long been linked to transcriptional control. The reversible acetylation of histones can result in chromatin remodeling and as such can act as a control mechanism for gene transcription. In general, hyperacetylation of histones facilitates gene expression, whereas histone deacetylation is correlated with transcriptional repression. Histone acetyltransferases were shown to act as transcriptional coactivators, whereas deacetylases were found to belong to transcriptional repression pathways.

The dynamic equilibrium between histone acetylation and deacetylation is essential for normal cell growth. Inhibition of histone deacetylation results in cell cycle arrest, cellular differentiation, apoptosis and reversal of the transformed phenotype.

Another group of proteins involved in the regulation of gene expression are the DNA methyltransferases (DNMT), which are responsible for the generation of genomic methylation patterns that lead to transcriptional silencing. DNA methylation is central to many mammalian processes including embryonic development, X-inactivation, genomic imprinting, and regulation of gene expression. DNA methylation in mammals is achieved by the transfer of a methyl group from S-adenosyl-methionine to the C5 position of cytosine. This reaction is catalyzed by DNA methyltransferases and is specific to cytosines in CpG dinucleotides. Seventy percent of all cytosines in CpG dinucleotides in the human genome are methylated and prone to deamination, resulting in a cytosine to thymine transition. This process leads to an overall reduction in the frequency of guanine and cytosine to about 40% of all nucleotides and a further reduction in the frequency of CpG dinucleotides to about a quarter of their expected frequency.

Four active DNA methyltransferases have been identified in mammals: DNMT1, DNMT2, DNMT3A and DNMT3B. In addition, DNMT3L is a protein that is closely related to DNMT3A and DNMT3B structurally and that is critical for DNA methylation, but appears to be inactive on its own. The methylation of cytosines in promoter regions containing CpG islands leads to the transcriptional inactivation of the downstream coding sequence in vertebrate cells.

A family of proteins known as methyl-CpG binding proteins (MBD 1 to 4) is thought to play an important role in methylation-mediated transcriptional silencing. MeCP2 was the first member of this family to be characterized and contains a methyl-CpG binding domain (MBD) and a transcriptional-repression domain (TRD), which facilitates an interaction with, and targets the Sin3A/HDAC complex to, methylated DNA. Like MeCP2, MBD1, MBD2, and MBD3 have been shown to be potent transcriptional repressors. MBD4 is a DNA glycosylase, which repairs G:T mismatches. Each member of this family, with the exception of MBD3, forms complexes with methylated DNA in mammalian cells, and all but MBD1 and MBD4 have been placed in known chromatin-remodeling complexes. Several proteins and protein complexes, such as the Mi-2 complex, couple DNA methylation to chromatin remodeling and histone deacetylation.

Another group of proteins involved in epigenetic regulation are histone methyltransferases (HMT), which are enzymes, histone-lysine N-methyltransferase and histone-arginine N-methyltransferase that catalyze the transfer of one to three methyl groups from the cofactor S-Adenosyl methionine to lysine and arginine residues of histone proteins. Methylated histones bind DNA more tightly, which inhibits transcription.

The structure of chromatin also can be altered through the activity of macromolecular assemblies known as chromatin remodeling complexes. See, for example, Cairns (1998) Trends Biochem. Sci. 23:20 25; Workman et al. (1998) Ann. Rev. Biochem. 67:545 579; Kingston et al. (1999) Genes Devel. 13:2339 2352 and Murchardt et al. (1999) J. Mol. Biol. 293:185 197. Chromatin remodeling complexes have been implicated in the disruption or reformation of nucleosomal arrays, resulting in modulation of transcription, DNA replication, and DNA repair (Bochar et al., (2000) PNAS USA 97(3): 1038 43). Many of these chromatin remodeling complexes have different subunit compositions, but all rely on ATPase enzymes for remodeling activity. There are also several examples of a requirement for the activity of chromatin remodeling complexes for gene activation in vivo.

The development of pluripotent or totipotent cells into a differentiated, specialized phenotype is determined by the particular set of genes expressed during development. Gene expression is mediated directly by sequence-specific binding of gene regulatory proteins that can effect either positive or negative regulation. However, the ability of any of these regulatory proteins to directly mediate gene expression depends, at least in part, on the accessibility of their binding site within the cellular DNA. As discussed above, accessibility of sequences in cellular DNA often depends on the structure of cellular chromatin within which cellular DNA is packaged.

Therefore, it would be useful to identify methods, compositions and kits that can induce the expression of genes required for pluripotency, including methods, compositions, and kits that can inhibit the activity, expression or both the activity and the expression of genes involved in repressing transcription.

BRIEF SUMMARY OF THE INVENTION

The invention relates to methods, compositions and kits for reprogramming a cell. Embodiments of the invention relate to methods comprising inducing the expression of a pluripotent or multipotent gene. In yet another embodiment, the invention further relates to methods comprising producing a reprogrammed cell. In still yet another embodiment, the invention relates to methods comprising inhibiting the expression of at least one gene that codes for a protein that is involved in transcriptional repression. The method further comprises inducing the expression of a pluripotent or multipotent gene, and reprogramming the cell.

Embodiments of the invention also relate to methods for reprogramming a cell comprising contacting a cell, a population of cells, a cell culture, a subset of cells from a cell culture, a homogeneous cell culture, or a heterogeneous cell culture, with an agent that impedes the expression of a gene that codes for a protein involved in transcriptional repression, inducing the expression of a pluripotent or multipotent gene, and reprogramming the cell. The method further comprises re-differentiating the reprogrammed cell.

An agent that impedes the expression of a gene that codes for a protein involved in transcriptional repression includes but is not limited to an shRNA molecule, an shRNAmir molecule, a combination of shRNA molecules, a combination of shRNAmir molecules, and a combination of shRNA and shRNAmir molecules.

Any gene that codes for a protein involved in transcriptional repression can be inhibited by the methods of the invention including but not limited to genes coding for DNA methyltransferases, histone deacetylases, histone acetyltransferase, lysine methyltransferase, histone demethylase, lysine demethylase, sirtuin, sirtuin activator, methyl binding domain proteins, histone methyltransferases, components of the SWI/SNF complex, components of the NuRD complex, and components of the INO80 complex. A single gene or more than one gene can be inhibited by the methods of the invention including but not limited to 2, 3, 4, 5, 6, 7, 8, 9, 10, 11-20, 21-30, 31-40, 41-50, and greater than 50 genes.

In another embodiment, the invention relates to a method for reprogramming comprising: exposing a cell to a shRNA construct that interferes with the expression of a gene that codes for a regulatory protein, inducing expression of a pluripotent or multipotent gene; and selecting a cell, wherein differentiation potential has been restored to said cell.

In still another embodiment, the invention relates to a method comprising exposing a cell with a first phenotype to a shRNA construct that interferes with the expression of a gene that codes for a regulatory protein; comparing the first phenotype of the cell to a phenotype obtained after exposing the cell to said shRNA construct, and selecting a cell that has been reprogrammed. In yet another embodiment, the method comprises comparing the genotype of a cell prior to exposing the cell to said shRNA construct to a genotype of the cell obtained after exposing said cell to said shRNA construct. In still yet another embodiment, the method comprises comparing the phenotype and genotype of a cell prior to exposing the cell to an shRNA construct to the phenotype and genotype of the cell after exposing the cell to said shRNA construct.

In still another embodiment, the method comprises culturing or expanding the selected cell to a population of cells. In yet another embodiment, the method comprises isolating a cell using an antibody that binds to a protein coded for by a pluripotent or multipotent gene or an antibody that binds to a multipotent marker or a pluripotent marker, including but not limited to SSEA3, SSEA4, Tra-1-60, and Tra-1-81. Cells may also be isolated using any method efficient for isolating cells including but not limited to a fluorescent cell activated sorter, immunohistochemistry, and ELISA. In another embodiment, the method comprises selecting a cell that has a less differentiated state than the original cell.

In still another embodiment, the invention further comprises comparing chromatin structure of a pluripotent or multipotent gene prior to exposure to said shRNA construct to the chromatin structure obtained after exposure to said agent.

In another embodiment, the invention relates to a method for reprogramming a cell comprising: exposing a cell with a first transcriptional pattern to a shRNA construct; inducing expression of a pluripotent or multipotent gene; comparing the first transcriptional pattern of the cell to a transcriptional pattern obtained after exposure to said shRNA construct and selecting a cell, wherein differentiation potential has been restored to said cell.

In still another embodiment, selecting a cell comprises identifying a cell with a transcriptional pattern that is at least 5-10%, 10-20%, 20-30%, 30-40%, 40-50%, 50-60%, 60-70%, 70-80%, 80-90%, 90-94%, 95%, or 95-99% similar to an analyzed transcriptional pattern of an embryonic stem cell. The entire transcriptional pattern of an embryonic stem cell need not be compared, although it may. Instead, a subset of embryonic genes may be compared including but not limited to 1-5, 5-10, 10-25, 25-50, 50-100, 100-200, 200-500, 500-1,000, 1,000-2,000, 2,000-2,500, 2,500-5,000, 5,000-10,000 and greater than 10,000 genes. The transcriptional patterns may be compared in a binary fashion, i.e., the comparison is made to determine if the gene is transcribed or not. In another embodiment, the rate and/or extent of transcription for each gene or a subset of genes may be compared. Transcriptional patterns can be determined using any methods known in the art including but not limited to RT-PCR, quantitative PCR, a microarray, southern blot and hybridization.

In yet another embodiment, at least one shRNA or shRNAmir sequence can be used to inhibit the expression of a DNA methyltransferases, a histone deacetylase, a methyl binding domain protein, or a histone methyltransferase. In still yet another embodiment, more than one shRNA or shRNAmir can be used to inhibit the expression of more than one protein involved in transcriptional repression including but not limited to a DNA methyltransferase, a histone deacetylase, a methyl binding domain protein, or a histone methyltransferase.

In yet another embodiment, the invention relates to a method for reprogramming a cell comprising: exposing a cell to an shRNA construct that interferes with the expression of a gene that codes for a first regulatory protein; exposing said cell to a second agent that inhibits the activity, expression or expression and activity of a second regulatory protein, wherein said second regulatory protein has a distinct function from the first regulatory protein, inducing expression of a pluripotent or multipotent gene, and selecting a cell, wherein differentiation potential has been restored to said cell. In another embodiment, the cell or population of cells may be exposed to the first and second agents simultaneously or sequentially. The second agent includes but is not limited to a small molecule, a small molecule inhibitor, a small molecule activator, a nucleic acid sequence, and an shRNA construct.

Embodiments of the invention also include methods for treating a variety of diseases using a reprogrammed cell produced according to the methods disclosed herein. In yet another embodiment, the invention also relates to therapeutic uses for reprogrammed cells and reprogrammed cells that have been re-differentiated.

Embodiments of the invention also relate to a method comprising screening for genes involved in reprogramming a cell. In yet another embodiment, the method further comprises screening for genes that code for proteins that inhibit transcription. In still yet another embodiment, the method comprises screening for genes that contribute to a cell being pluripotent or multipotent. The screen may be performed using an appropriate screening reagent including but not limited to a shRNA library or an shRNAmir library.

Embodiments of the invention also relate to a reprogrammed cell produced by the methods of the invention. The reprogrammed cell can be re-differentiated into a single lineage or more than one lineage. The reprogrammed cell can be multipotent or pluripotent.

In yet another embodiment, the invention relates to an enriched population of reprogrammed cells produced according to a method comprising the steps of: exposing a cell to a shRNA construct that induces expression of a pluripotent or multipotent gene; and selecting a cell, wherein differentiation potential has been restored to said cell, and culturing said selected cell to produce population of cells. In still another embodiment, the reprogrammed cell expresses a cell surface marker selected from the group consisting of: SSEA3, SSEA4, Tra-1-60, and Tra-1-81. In still another embodiment, the reprogrammed cell can be selected through expression of a protein from a pluripotent or multipotent gene including but not limited to Oct-3/4, Sox-2, Nanog, and Klf4. In yet another embodiment, the reprogrammed cells account for at least 5-10%, 10-20%, 20-30%, 30-40%, 40-50%, 50-60%, 60-70%, 70-80%, 80-90%, 90-95%, 96-98%, or at least 99% of the enriched population of cells.

Embodiments of the invention also relate to kits for preparing the methods and compositions of the invention. The kit can be used for, among other things, reprogramming a cell and generating ES-like and stem cell-like cells.

BRIEF DESCRIPTION OF THE DRAWINGS

FIG. 3A is a graph reporting the increase in expression of Oct-4 and decrease in expression of DNMT1 in fetal human dermal fibroblast cells infected with DNMT1 shRNA FIG. 3B is a graph reporting the increase in expression of Oct-4 and decrease in expression of DNMT1 in fetal human dermal fibroblast cells infected with DNMT1 shRNA and cultured in presence of puromycin.

FIG. 3C is a graph reporting the increase in expression of Oct-4 and decrease in expression of DNMT1 in fetal human dermal fibroblast cells infected with DNMT1 shRNA and cultured in presence of puromycin and hES culture.

DETAILED DESCRIPTION OF THE PREFERRED EMBODIMENT

Definitions

Figure 1A:
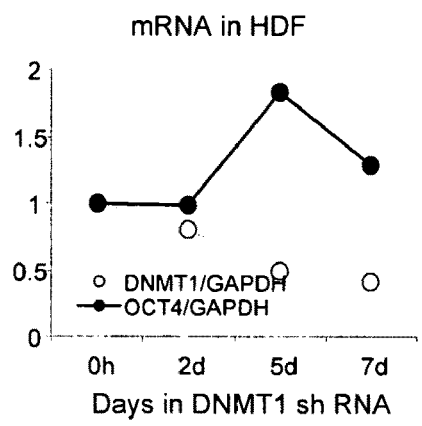
FIG. 1A is a graph reporting the increase in expression of Oct-4 and decrease in expression of DNMT1 in cells infected with DNMT1 shRNA.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

"Cell" or "cells," unless specifically limited to the contrary, includes any somatic cell, embryonic stem (ES) cell, adult stem cell, an organ specific stem cell, nuclear transfer (NT) units, and stem-like cells. The cell or cells can be obtained from any organ or tissue. The cell or cells can be human or other animal. For example, a cell can be mouse, guinea pig, rat, cattle, horses, pigs, sheep, goats, etc. A cell also can be from non-human primates.

"Culture Medium" or "Growth Medium" means a suitable medium capable of supporting growth of cells.

"Differentiation" means the process by which cells become structurally and functionally specialized during embryonic development.

"DNA Methylation" means the attachment of a methyl group (a —CH3 group) to a cytosine. This is done routinely, as a way to protect self DNA from the enzymes and chemicals produced to destroy foreign DNA, and as a way to regulate transcription of genes in the DNA.

"Epigenetics" means the state of DNA with respect to heritable changes in function without a change in the nucleotide sequence. Epigenetic changes can be caused by modification of the DNA, such as by methylation and demethylation, without any change in the nucleotide sequence of the DNA.

"Histone" means a class of protein molecules found in chromosomes responsible for compacting DNA enough so that it will fit within a nucleus.

"Inhibiting or interfering with the expression of a gene" means reducing the expression of a gene. In some embodiments, such reduction of gene expression is at least about 5-25%, more preferably at least about 50%, still more preferably at least about 75%, and still yet more preferably at least about 90%. In other embodiments, gene expression is reduced by at least 95% and in yet another embodiment, gene expression is reduced by at least 99%.

"Knock down" means to suppress the expression of a gene in a gene-specific fashion. A cell that has one or more genes "knocked down," is referred to as a knock-down organism or simply a "knock-down."

"Pluripotent" means capable of differentiating into cell types of the 3 germ layers or primary tissue types.

"Pluripotent gene" means a gene that contributes to a cell being pluripotent.

"Pluripotent cell cultures" are said to be "substantially undifferentiated" when that display morphology that clearly distinguishes them from differentiated cells of embryo or adult origin. Pluripotent cells typically have high nuclear/cytoplasmic ratios, prominent nucleoli, and compact colony formation with poorly discernable cell junctions, and are easily recognized by those skilled in the art. It is recognized that colonies of undifferentiated cells can be surrounded by neighboring cells that are differentiated. Nevertheless, the substantially undifferentiated colony will persist when cultured under appropriate conditions, and undifferentiated cells constitute a prominent proportion of cells growing upon splitting of the cultured cells. Useful cell populations described in this disclosure contain any proportion of substantially undifferentiated pluripotent cells having these criteria. Substantially undifferentiated cell cultures may contain at least about 20%, 40%, 60%, or even 80% undifferentiated pluripotent cells (in percentage of total cells in the population).

"Regulatory protein" means any protein that regulates a biological process, including regulation in a positive and negative direction. The regulatory protein can have direct or indirect effects on the biological process, and can either exert affects directly or through participation in a complex.

"Reprogramming" means removing epigenetic marks in the nucleus, followed by establishment of a different set of epigenetic marks. During development of multicellular organisms, different cells and tissues acquire different programs of gene expression. These distinct gene expression patterns appear to be substantially regulated by epigenetic modifications such as DNA methylation, histone modifications and other chromatin binding proteins. Thus each cell type within a multicellular organism has a unique epigenetic signature which is conventionally thought to become "fixed" and immutable once the cells differentiate or exit the cell cycle. However, some cells undergo major epigenetic "reprogramming" during normal development or certain disease situations.

"Totipotent" means capable of developing into a complete embryo or organ.

Embodiments of the invention relate to methods comprising inducing expression of at least one gene that contributes to a cell being pluripotent or multipotent. In another embodiment, the invention relates to methods comprising inducing the expression of at least one gene that contributes to a cell being multipotent. In some embodiments, the methods comprise inducing the expression of at least one gene that contributes to a cell being pluripotent or multipotent and producing reprogrammed cells that are pluripotent or multipotent and are capable of directed differentiation into multiple lineages.

Embodiments of the invention also relate to a method comprising modifying chromatin structure, and reprogramming a cell to be pluripotent or multipotent. In yet another embodiment, modifying chromatin structure comprises inhibiting the expression of at least one gene that codes for a protein involved in a repression complex.

In another embodiment, the method comprises inhibiting the expression of at least one gene that codes for a protein involved in transcriptional repression, and inducing expression of at least one gene that contributes to a cell being pluripotent or multipotent. In yet another embodiment, the method comprises inhibiting the expression of at least one gene that codes for a protein involved in transcriptional repression and producing a reprogrammed cell. The methods of the invention can inhibit the expression of a gene that codes for a protein involved in any type of repression including but not limited to active repressors, repressors that modify the basal transcriptional machinery, proteins that modify structures to recruit repressors, proteins that recruit repressors, proteins that modify nucleosomes or chromatin structure, proteins that modify histones, proteins that modify DNA, and proteins that are involved in chromatin remodeling complexes.

In still another embodiment, the invention relates to a method for reprogramming a cell comprising: exposing a cell to a shRNA construct that interferes with expression of gene that codes for a regulatory protein, inducing expression of a pluripotent or multipotent gene; and selecting a cell, wherein differentiation potential has been restored to said cell. The pluripotent or multipotent gene may be induced by any fold increase in expression including but not limited to 0.25-0.5, 0.5-1, 1.0-2.5, 2.5-5, 5-10, 10-15, 15-20, 20-40, 40-50, 50-100, 100-200, 200-500, and greater than 500. In another embodiment, the method comprises plating differentiated cells, exposing said differentiated cell to a shRNA construct that interferes with expression of a gene that codes for a regulatory protein, culturing said cells, and identifying a cell that has been reprogrammed. The shRNA construct can interfere with the expression of the regulatory protein in any amount including but not limited to 1-5%, 5-10%, 10-20%, 20-30%, 30-40%, 40-50%, 50-60%, 60-70%, 70-80%, 80-90%, 90-95%, and 95-99%, 99-200%, 200-300%, 300-400%, 400-500% and greater than 500%.

In yet another embodiment, the method further comprises selecting a cell using an antibody directed to a protein or a fragment of a protein coded for by a pluripotent or multipotent gene or a pluripotent or multipotent surface marker. Any type of antibody can be used including but not limited to a monoclonal, a polyclonal, a fragment of an antibody, a peptide mimetic, an antibody to the active region, and an antibody to the conserved region of a protein. In still another embodiment, the method comprises selecting a cell and expanding or culturing said cell to a pluripotent cell culture or a multipotent cell culture.

In still another embodiment, the method further comprises selecting a cell using a reporter driven by a pluripotent or mulitpotent gene or a pluripotent or mulitpotent surface marker. Any type of reporter can be used including but not limited to a fluorescent protein, green fluorescent protein, cyan fluorescent protein (CFP), a yellow fluorescent protein (YFP), bacterial luciferase, jellyfish acquorin, enhanced green fluorescent protein, turbo GFP, chloramphenicol acetyltransferase (CAT), dsRED, β-galactosidase, and alkaline phosphatase.

In still another embodiment, the method further comprises selecting a cell using resistance as a selectable marker including but not limited to resistance to an antibiotic, a fungicide, puromycin, hygromycin, dihydrofolate reductase, thymidine kinase, neomycin resistance (neo), G418 resistance, mycophenolic acid resistance (gpt), zeocin resistance protein and streptomycin.

In still another embodiment, the method further comprises comparing the chromatin structure of a pluripotent or multipotent gene of a cell, prior to exposing said cell to an shRNA construct, to the chromatin structure of a pluripotent or multipotent gene obtained after treatment with said shRNA construct. Any aspect of chromatin structure can be compared including but not limited to euchromatin, heterochromatin, histone acetylation, histone methylation, the presence and absence of histone or histone components, the location of histones, the arrangement of histones, and the presence or absence of regulatory proteins associated with chromatin. The chromatin structure of any region of a gene may be compared including but not limited to an enhancer element, an activator element, a promoter, the TATA box, regions upstream of the start site of transcription, regions downstream of the start site of transcription, exons and introns.

Inhibiting the expression of a gene that codes for a protein involved in transcriptional repression can be accomplished by any appropriate mechanism including but not limited to RNA interference (RNAi). RNAi regulates gene expression via a ubiquitous mechanism by degradation of target mRNA in a sequence-specific manner. Small interfering RNA strands (siRNA) are key to the RNAi process, and have complementary nucleotide sequences to the targeted RNA strand. Specific RNAi pathway proteins are guided by the siRNA to the targeted messenger RNA (mRNA), where they "cleave" the target, breaking it down into smaller portions that can no longer be translated into protein.

In yet another embodiment, the method comprises contacting a cell with a short hairpin RNA (shRNA) and inhibiting the expression of at least one gene that codes of a protein involved in transcriptional repression. In yet another embodiment, the method further comprises producing a reprogrammed cell. The reprogrammed cell can be pluripotent or multipotent.

shRNA is a sequence of RNA that makes a tight hairpin turn that can be used to silence gene expression; the use of shRNA is one approach to achieve RNA interference. In some embodiments, shRNA can be incorporated into a vector with a promoter, including but not limited to a U6 promoter, to ensure that the shRNA is expressed. The vector is usually passed on to daughter cells, allowing the gene silencing to be inherited. The shRNA hairpin structure is cleaved by the cellular machinery into short interfering RNA, which then is bound to the RNA-induced silencing complex (RISC). This complex binds to and cleaves mRNAs that match the siRNA that is bound to it.

The shRNA can be incorporated into a lentiviral construct. Lentivirus is a genus of slow viruses of the Retroviridae family, characterized by a long incubation period. Lentiviruses can deliver a significant amount of genetic information into the DNA of the host cell, and thus, are an efficient method of a gene delivery vector.

In another embodiment, an shRNA library can be used with the methods of the invention to identify factors involved in transcriptional repression, factors involved in chromatin remodeling, and factors that contribute to a cell being pluripotent or multipotent. In still another embodiment, the shRNA library can be from the The RNAi Consortium (TRC), which is a collaborative group of 11 world-renowned academic and corporate life science research groups whose mission is to create comprehensive tools for functional genomics research and make them broadly available to scientists worldwide. The TRC collection, developed at the Broad Institute of MIT and Harvard, currently consists of 159,000 pre-cloned shRNA constructs targeting 16,000 annotated human genes.

shRNA constructs, libraries and vectors can be custom made or can be purchased from commercial sources including but not limited to SMARTvector shRNA Lentiviral technology available from Dharmacon RNAi technologies (Thermo Scientific, Lafayette, Colo.), MISSION™ TRC shRNA, which is available from Sigma Aldrich (St. Louis, Mo.), TRC lentiviral shRNA library, which is available from Open Biosystems (Huntsville, Ala.), BLOCK-iT™ RNAi vectors that feature constitutive or inducible promoters, different selection markers, and viral delivery options, available with Lentiviral and Adenoviral vectors (Invitrogen, Carlsbad, Calif.).

Further, shRNA molecules directed toward specific targets also are available from commercial sources such as OriGene (Rockville, Md.), and Santa Cruz Biotechnology (Santa Cruz, Calif.). An inducible shRNA also is available from Clonetech (Mountainview, Calif.). The Knockout Inducible RNAi Systems tightly regulates the expression of functional short hairpin RNAs (shRNAs) in mammalian cells for the purpose of silencing target genes. Knockout Inducible RNAi Systems are useful in cases where suppression of a gene may be lethal, preventing its analysis. There are several versions available: The Knockout Single Vector Inducible RNAi system and The Knockout Tet RNAi Systems H and P.

In another embodiment, the method comprises contacting a cell with an shRNAmir and inhibiting the expression of at least one gene involved in transcriptional repression. In yet another embodiment, the method further comprises producing a reprogrammed cell. The reprogrammed cell can be pluripotent or multipotent.

microRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

shRNAmir triggers for mammalian RNAi are based on current knowledge of the endogenous microRNA biogenesis pathway. shRNAmir constructs are designed to mimic a natural microRNA primary transcript, enabling specific processing by the endogenous RNAi pathway and producing effective gene knockdown. Genome wide shRNAmir libraries incorporate several features aimed at increasing the efficiency and specificity of gene knockdown providing solutions for diverse RNAi applications.

An shRNAmir library can be used with the methods of the invention. In still another embodiment, the shRNAmir library can be from the The RNAi Consortium (TRC).

The shRNAmir and shRNAmir library can be custom made or purchased from a commercial source. For instance, the Expression Arrest™ microRNA-adapted shRNA (shRNAmir libraries), retroviral shRNAmir libraries, lentiviral shRNAmir libraries, TRIPz lentiviral inducible shRNAmir libraries, pSM2 retroviral shRNAmir libraries are all available from Open Biosystems (Huntsville, Ala.).

In another embodiment, the methods of the invention further comprises contacting a cell with an shRNA, an shRNA library, an shRNAmir, an shRNAmir library or a combination of the shRNA constructs, inhibiting the expression or activity of at least one gene involved in transcriptional repression and identifying said gene that has been inhibited.

A single shRNA, or shRNAmir can be used to target the inhibition of a single gene or more than one shRNA or shRNAmir can be used to target the inhibition of a single gene. In yet another embodiment, a single shRNA or shRNAmir can be used to target the inhibition of more than one gene. In still yet another embodiment, more than one shRNA or more than shRNAmir can be used to target the inhibition of more than one gene. Mixtures of shRNA constructs and shRNAmir constructs can be used. A single gene or more than one gene can be inhibited by the methods of the invention including but not limited to 2, 3, 4, 5, 6, 7, 8, 9, 10, 11-20, 21-30, 31-40, 41-50, and greater than 50 genes.

Any gene coding for a protein involved in repression of gene expression can be inhibited by the methods of the invention including but not limited to a histone deacetylase, a methyl binding domain protein, a methyl adenosyltransferase, a DNA methyltransferase, a histone methyltransferase, and a methyl cycle enzyme, nuclear receptors, orphan nuclear receptors, Esrrβ and EssRγ. A representative list of genes that may be inhibited by the methods of the invention is provided n Table I.

For example, a methyl binding domain protein, e.g., MeCP2, binds to methylated cytosines and recruits histone deacetylases that then deacetylate histone proteins, resulting in a condensed chromatin structure, which inhibits transcription. The methods of the invention can inhibit the expression of a gene that codes for a protein in repressive complexes, and thereby induce transcription of pluripotency genes.

TABLE I

Representative list of Genes involved in repression and repression complexes

| Histone Deacetylases | Methyl Binding Domain Proteins | Meth. Adenosyl-transferases | DNA Methyl-transferases | Histone Methyl-transferase | Methyl Cycle Enzymes |
|---|---|---|---|---|---|
| Class 1 (HDACs 1-3, 8, 11) | MBD1 | MAT2A | DNMT1 | EHMT1 | MTHFR |
| Class II (HDACs 4-7, 9, 10) | MBD2 | MAT1A | DNMT2 | HDM G9A | CBS |
| Class III (SIRT1 1-7) | MBD3 | MAT2B | DNMT3B | SUV39H1 | |
| Class IV (HDAC 11) | MBD4 | | DNMT3A | SETDB1 | |
| | MeCP2 | | DNMT3L | | |

For instance, an shRNAmir can be used to inhibit the expression of MeCP2, thereby significantly reducing the recruitment of HDACs to chromatin structure. This can lead to the up-regulation of genes critical for a cell to be pluripotent or multipotent and thereby increase differentiation capacity in somatic cells. Similarly, an shRNAmir can be used to inhibit an HDAC, which would similarly lead to the up-regulation of genes critical for pluripotency. Moreover, an shRNAmir directed toward a DNA methyltransferase, an shRNAmir directed toward a methyl binding protein, and an shRNAmir directed toward an HDAC can be used simultaneously or sequentially to inhibit the expression of genes that code for proteins in repression complexes. The above discussion is meant for illustrative purposes only and should not be construed to limit the scope of the invention.

Genes coding for proteins in other complexes involved in chromatin remodeling also can be inhibited by methods of the invention including but not limited to the SWI/SNF complex, the NuRD complex, the Mi-2 complex, the Sin3 complex, and INO80. The hSWI/SNF complex is a multisubunit protein complex that is known to play a key role in regulation of chromatin accessibility. Any component of the hSWI/SNF complex can be inhibited by the methods of the invention including but not limited to SNF5/INI1, BRG1, BRM, BAF155, and BAF170. SWI/SNF was originally identified in yeast as required for activation of a variety of genes. The hSWI/SNF complexes have been shown to be essential for regulation of several developmentally specific gene expression programs.

Any component of the Sin3 complex can be inhibited by the methods of the invention including but not limited to HDAC1, HDAC2, RbAp46, RbAp48, Sin3A, SAP30, and SAP18.

Any component of the NuRD complex can be inhibited by the methods of the invention including but not limited to Mi2, p70, and p32.

Any component of the INO80 complex can be inhibited by the methods of the invention including but not limited to Tip49A, Tip49B, the SNF2 family helicase Ino80, actin related proteins ARP4, ARP5, and Arp8, YEATS domain family member Taf14, HMG-domain protein, Nhp10, and six additional proteins designated Ies1-6.

Any number of shRNA or shRNAmir sequences can be used to induce the expression of gene that contribute to a cell being pluripotent or multipotent including but not limited to 1-5, 6-10, 11-15, 16-20, 21-25, 26-30, 31-35, 36-40, 41-45, 46-50, and greater than 50 shRNA or shRNAmir sequences.

A reprogrammed cell produced by the methods of the invention can be pluripotent or multipotent. A reprogrammed cell produced by the methods of the invention can have a variety of different properties including embryonic stem cell like properties. For example, a reprogrammed cell may be capable of proliferating for at least 10, 15, 20, 30, or more passages in an undifferentiated state. In other forms, a reprogrammed cell can proliferate for more than a year without differentiating. Reprogrammed cells can also maintain a normal karyotype while proliferating and/or differentiating. Some reprogrammed cells also can be cells capable of indefinite proliferation in vitro in an undifferentiated state. Some reprogrammed cells also can maintain a normal karyotype through prolonged culture. Some reprogrammed cells can maintain the potential to differentiate to derivatives of all three embryonic germ layers (endoderm, mesoderm, and ectoderm) even after prolonged culture. Some reprogrammed cells can form any cell type in the organism. Some reprogrammed cells can form embryoid bodies under certain conditions, such as growth on media that do not maintain undifferentiated growth. Some reprogrammed cells can form chimeras through fusion with a blastocyst, for example.

Reprogrammed cells can be defined by a variety of markers. For example, some reprogrammed cells express alkaline phosphatase. Some reprogrammed cells express SSEA-1, SSEA-3, SSEA-4, TRA-1-60, and/or TRA-1-81. Some reprogrammed cells express Oct 4, Sox2, and Nanog. It is understood that some reprogrammed cells will express these at the mRNA level, and still others will also express them at the protein level, on for example, the cell surface or within the cell.

A reprogrammed cell can have any combination of any reprogrammed cell property or category or categories and properties discussed herein. For example, a reprogrammed cell can express alkaline phosphatase, not express SSEA-1, proliferate for at least 20 passages, and be capable of differentiating into any cell type. Another reprogrammed cell, for example, can express SSEA-1 on the cell surface, and be capable of forming endoderm, mesoderm, and ectoderm tissue and be cultured for over a year without differentiation.

A reprogrammed cell can be alkaline phosphatase (AP) positive, SSEA-1 positive, and SSEA-4 negative. A reprogrammed cell also can be Nanog positive, Sox2 positive, and Oct-4 positive. A reprogrammed cell also can be Tcl1 positive, and Tbx3 positive. A reprogrammed cell can also be Cripto positive, Stellar positive, Daz1 positive or Fragilis positive. A reprogrammed cell can express cell surface antigens that bind with antibodies having the binding specificity of monoclonal antibodies TRA-1-60 (ATCC HB-4783) and TRA-1-81 (ATCC HB-4784). Further, as disclosed herein, a reprogrammed cell can be maintained without a feeder layer for at least 10, 11, 12, 13, 14, 15, 16, 17, 18, 19, 20, 20-25, 26-30, 31-40, 41-50, 51-60, 61-70, 71-80, 81-90, 91-100 passages or for over a year.

A reprogrammed cell may have the potential to differentiate into a wide variety of cell types of different lineages including fibroblasts, osteoblasts, chondrocytes, adipocytes, skeletal muscle, endothelium, stroma, smooth muscle, cardiac muscle, neural cells, hemiopoetic cells, pancreatic islet, or virtually any cell of the body. A reprogrammed cell may have the potential to differentiate into any number of lineages including 1, 2, 3, 4, 5, 6-10, 11-20, 21-30, and greater than 30 lineages.

Any gene that contributes to a cell being pluripotent or multipotent may be induced by the methods of the invention including but not limited to glycine N-methyltransferase (Gnmt), Octamer-4 (Oct4), Nanog, SRY (sex determining region Y)-box 2 (also known as Sox2), Myc, REX-1 (also known as Zfp-42), Integrin α-6, Rox-1, LIF-R, TDGF1 (CRIPTO), Fragilis, SALL4 (sal-like 4), GABRB3, LEFTB, NR6A1, PODXL, PTEN, Leukocyte cell derived chemotaxin 1 (LECT1), BUB1, and Krüppel-like factors (Klf) such as Klf4 and Klf5. Any number of genes that contribute to a cell being pluripotent or multipotent can be induced by the methods of the invention including but not limited to 1, 2, 3, 4, 5, 6, 7, 8, 9, 10, 11-20, 21-30, 31-40, 41-50, and greater than 50 genes.

Further, Ramalho-Santos et al. (Science 298, 597 (2002)), Ivanova et al. (Science 298, 601 (2002)) and Fortunel et al. (Science 302, 393b (2003)) each compared three types of stem cells and identified a list of commonly expressed "stemness" genes, proposed to be important for conferring the functional characteristics of stem cells (all of the above-cited references are incorporated in their entirety). Any of the genes identified in the above-mentioned studies may be induced by the methods of the invention. Table II provides a list of genes thought to be involved in conferring the functional characteristics of stem cells. In addition to the genes listed in Table II, 93 expressed sequence tags (EST) clusters with little or no homology to known genes were also identified by Ramalho-Santos et al. and Ivanova et al., and are included within the methods of the invention.

TABLE II

Genes implicated in conferring stem cell characteristics

| Symbol | Gene | Function |
|---|---|---|
| F2r | Thrombin receptor | G-protein coupled receptor, coagulation cascade, required for vascular development |
| Ghr | Growth hormone receptor | Growth hormone receptor/binding protein, activates Jak2 |
| Itga6 | Integrin alpha 6 | cell adhesion, cell-surface mediated signalling, can combine with Integrin b1 |
| Itgb1 | Integrin beta 1 (fibronectin Receptor) | cell adhesion, cell-surface mediated signalling, can combine with Integrin a6 |
| Adam 9 | A disintegrin and metalloproteinase domain 9 (meltrin gamma) | cell adhesion, extracellular proteolysis, possible fusogenic function |
| Bys | Bystin-like (Bystin) | cell adhesion, may be important for embryo implantation (placenta) |
| Ryk | Receptor-like tyrosine kinase | unconventional receptor tyrosine kinase |
| Pkd2 | Polycystic kidney disease 2 | calcium channel |
| Kcnab3 | Potassium voltage gated channel, shaker related subfamily, beta member 3 | regulatory subunit of potassium channel |
| Gnb1 | Guanine nucleotide binding protein beta 1 | G-protein coupled receptor signaling |
| Gab1 | Growth factor receptor bound protein 2 (Grb2) - associated protein 1 | integration of multiple signaling pathways |
| Kras2 | Kirsten rat sarcoma oncogene 2 | binds GTP and transmits signals from growth factor receptors |
|  | ESTs highly similar to Ras p21 protein activator (Gap) | suppressor of RAS function |
| Cttn | Cortactin | regulates actin cytoskeleton, overexpressed in tumors |
| Cops4 | COP9 (constitutive photomorphogenic), subunit 4 | Cop9 signalosome, integration of multiple signaling pathways, regulation of protein degradation |
| Cops7a | COP9 (constitutive photomorphogenic), subunit 7a | Cop9 signalosome, integration of multiple signaling pathways, regulation of protein degradation |
| Madh1 | Mad homolog 1 (Smad1) | TGFb pathway signal transducer |
| Madh2 | Mad homolog 2 (Smad2) | TGFb pathway signal transducer |
| Tbrg1 | TGFb regulated 1 | induced by TGFb |
| Stam | signal transducing adaptor molecule (SH3 domain and ITAM motif) 1 | associates with Jak tyrosine kinase |
| Statip1 | STAT interacting protein 1 | scaffold for Jak/Stat3 binding |
| Cish2 | Cytokine inducible SH2- containing protein 2 (Ssi2) | STAT induced STAT inhibitor-2, interacts with Igf1R |
|  | ESTs moderately similar to Jak3 | possible tyrosine kinase |
|  | ESTs highly similar to PPP2R1B | regulatory subunit of protein phosphatase 2, putative tumor suppressor |

TABLE II-continued

Genes implicated in conferring stem cell characteristics

| Symbol | Gene | Function |
| --- | --- | --- |
| Rock2 | Rho-associated coiled-coil forming kinase 2 | serine/theonine kinase, target of Rho |
| Yes | Yamaguchi sarcoma viral oncogene homolog | intracellular tyrosine kinase, proto-oncogene, Src family |
| Yap | Yes-associated protein 1 | bind Yes, transcriptional co-activator |
| Ptpn2 | Protein tyrosine non-receptor phosphatase 2 | dephosphorylates proteins |
| Ppp1r2 | Protein phosphatase 1, regulatory (inhibitor) 2 | Inhibitory subunit of protein phosphatase 1 |
| Ywhab | Tyrosine/tryptophan monooxgenase activation protein beta (14-3-3beta) | Binds phosphoserine-proteins, PKC pathway |
| Ywhah | Tyrosine/tryptophan monooxgenase activation protein eta (14-3-3eta) | Binds phosphoserine-proteins, PKC pathway |
| Axo | Axotrophin | contains a PHD domain, an adenylaye cyclase domain and a consensus region for G-protein interaction, required for neuronal maintenance |
| Trip6 | Thyroid hormone receptor interactor 6 | interacts with THR in the presence of TH, putative co-activator for Rel transcription factor |
| Gfer | Growth factor, erv1 (S. cerevisiae)-like (augmenter of liver regeneration) | sulphydryl oxidase, promotes liver regeneration, stimulates EGFR and MAPK pathways |
| Upp | Uridine phosphorylase | interconverts uridine and uracil, highly expressed in transformed cells, may produce 2-deoxy-D-ribose, a potent angiogenic factor |
| Mdfi | MyoD family inhibitor | inhibitor of bHLH and beta-catenin/TCF transcription factors |
| Tead2 | TEA domain 2 | transcriptional factor |
| Yap | Yes-associated 65 kD | Binds Yes, transcriptional co-activator |
| Fhl1 | Four and a half LIM | may interact with RBP-J/Su(H) |
| Zfx | Zinc Finger X-linked | zinc finger, putative transcription factor |
| Zfp54 | Zinc finger 54 | zinc finger, putative transcription factor |
|  | Zinc finger protein | zinc finger, putative transcription factor |
| D17Ertd197e | D17Ertd197e | zinc finger, putative transcription factor |
|  | ESTs, high similarity to Zfp | zinc finger, putative transcription factor |
|  | ESTs, high similarity to Zfp | zinc finger, putative transcription factor |
|  | ESTs, high similarity to Zfp | zinc finger, putative transcription factor |
| Rnf4 | RING finger 4 | steroid-mediated transcription |
| Chd1 | Chromodomain helicase DNA binding protein 1 | modification of chromatin structure, SNF2/SW12 family |
| Etl1 | enhancer trap locus 1 | modification of chromatin structure, SNF2/SW12 family |
| Rmp | Rpb5-mediating protein | Binds RNA, PolII, inhibits transcription |
| Ercc5 | Excision repair 5 | endonuclease, repair of UV-induced damage |
| Xrcc5 | X-ray repair 5 (Ku80) | helicase, involved in V(D)J recombination |
| Msh2 | MutS homolog 2 | mismatch repair, mutated in colon cancer |
| Rad23b | Rad23b homolog | excision repair |
| Ccnd1 | Cyclin D1 | G1/S transition, regulates CDk2 and 4, overexpressed in breast cancer, implicated in other cancers |
| Cdkn1a | Cdk inhibitor 1a P21 | inhibits G1/S transition, Cdk2 inhibitor, required for HSC maintenance |
| Cdkap1 | Cdk2 associated protein | binds DNA primase, possible regulator of DNA replication (S phase) |
| Cpr2 | Cell cycle progression 2 | overcomes G1 arrest in S. cerevisiae |
| Gas2 | Growth arrest specific 2 | highly expressed in growth arrested cells, part of actin cytoskeleton |
| CenpC | Centromere protein C | present in active centromeres |
| Wig1 | Wild-type p53 induced 1 | p53 target, inhibits tumor cell growth |
| Tmk | Thymidylate kinase | dTTP synthesis pathway, essential for S phase progression |
| Umps | Uridine monophosphate synthetase | Pyrimidine biosynthesis |
| Sfrs3 | Splicing factor RS rich 3 | implicated in tissue-specific differential splicing, cell cycle regulated |
|  | ESTs highly similar to exportin 1 | Cell cycle-regulated nuclear export protein |
|  | ESTs highly similar to CAD | trifunctional protein of pyrimidine biosynthesis, activated (phosphorylated) by MAPK |
|  | ESTs similar to Mapkkkk3 | Map kinase cascade |

TABLE II-continued

Genes implicated in conferring stem cell characteristics

| Symbol | Gene | Function |
|---|---|---|
| Gas2 | Growth arrest specific 2 | highly expressed in growth arrested cells, part of actin cytoskeleton, target of caspase-3, stabilizes p53 |
| Wig1 | Wild-type p53 induced 1 | p53 target, inhibits tumor cell growth |
| Pdcd2 | Programmed cell death 2 | unknown |
| Sfrs3 | Splicing factor RS rich 3 | implicated in tissue-specific differential splicing, cell cycle regulated |
| | ESTs highly similar to Sfrs6 | putative splicing factor |
| | ESTs highly similar to pre-mRNA splicing factor Prp6 | putative splicing factor |
| Snrp1c | Small nuclear ribonucleoprotein polypeptide C | U1 snRNPs, component of the spliceosome |
| Phax | Phosphorylated adaptor for RNA export | mediates U snRNA nuclear export |
| NOL5 | Nucleolar protein 5 (SIK similar) | pre-rRNA processing |
| | ESTs highly similar to Nop56 | pre-rRNA processing |
| Rnac | RNA cyclase | unknown |
| | ESTs highly similar to Ddx1 | DEAD-box protein, putative RNA helicase |
| Eif4ebp1 | Eukaryotic translation initiation factor 4E binding protein 1 | translational repressor, regulated (phosphorylated) by several signaling pathways |
| Eif4g2 | Eukaryotic translation initiation factor 4, gamma 2 | translational repressor, required for gastrulation and ESC differentiation |
| | ESTs highly similar to Eif3s1 | translation initiation factor |
| Mrps31 | Mitochondrial ribosomal protein S31 | component of the ribosome, mitochondria |
| Mrpl17 | Mitochondrial ribosomal protein L17 | component of the ribosome, mitochondria |
| Mrpl34 | Mitochondrial ribosomal protein L34 | component of the ribosome, mitochondria |
| Hspa1l | Heat shock 70 kD protein-like 1 (Hsc70t) | chaperone, testis-specific |
| Hspa4 | Heat shock 70 kDa protein 4 (Hsp110) | chaperone |
| Dnajb6 | DnaJ (Hsp40) homolog, subfamily B, member 6 (Mammalian relative of Dnaj) | co-chaperone |
| Hrsp12 | Heat responsive | possible chaperone |
| Tcp1-rs1 | T-complex protein 1 related sequence 1 | possible chaperone |
| Ppic | Peptidylprolyl isomerase C (cyclophilin C) | isomerization of peptidyl-prolyl bonds |
| Fkbp9 | FK506-binding protein 9 (63 kD) | possible peptidyl-prolyl isomerase |
| | ESTs moderately similar to Fkbp13 | possible peptidyl-prolyl isomerase |
| Ube2d2 | Ubiquitin-conjugating enzyme E2D2 | E2, Ubiquitination of proteins |
| Arih1 | Ariadne homolog | likely E3, Ubiquitin ligase |
| Fbxo8 | F-box only 8 | putative SCF Ubiquitin ligase subunit |
| | ESTs moderately similar to Ubc13 (bendless) | possible E2, Ubiquitination of proteins |
| Usp9x | Ubiquitin protease 9, X chromosome | removes ubiquitin from proteins |
| Uchrp | Ubiquitin c-terminal hydrolase related polypeptide | likely removes ubiquitin from proteins |
| Axo | Axotrophin | contains RING-CH domain similar to E3s, Ubiquitin ligases |
| Tpp2 | Tripeptidyl peptidase II | serine expopeptidase, associated with the proteasome |
| Cops4 | COP9 (constitutive photomorphogenic) subunit 4 | Cop9 signalosome, integration of multiple signaling pathways, regulation of protein degradation |
| Cops 7a | COP9 (constitutive photomorphogenic), subunit 7a | Cop9 signalosome, integration of multiple signaling pathways, regulation of protein degradation |
| | ESTs highly similar to proteasome 26S subunit, non-ATPase, 12 (p55) | regulatory subunit of the proteasome |

TABLE II-continued

Genes implicated in conferring stem cell characteristics

| Symbol | Gene | Function |
| --- | --- | --- |
| Nyren18 | NY-REN-18 antigen (NUB1) | interferon-9 induced, downregulator of Nedd8, a ubiquitin-like protein |
| Rab18 | Rab18, member RAS oncogene family | small GTPase, may regulate vesicle transport |
| Rabggtb | RAB geranlygeranyl transferase, b subunit | regulates membrane association of Rab proteins |
| Stxbp3 | Syntaxin binding protein 3 | vesicle/membrane fusion |
| Sec23a | Sec23a (S. cerevisiae) | ER to Golgi transport |
|  | ESTs moderately similar to Coatomer delta | ER to Golgi transport |
| Abcb1 | Multi-drug resistance 1 (Mdr1) | exclusion of toxic chemicals |
| Gsta4 | Glutathione S-transferase 4 | response to oxidative stress |
| Gslm | Glutamate-cycteine ligase modifier subunit | glutathione biosynthesis |
| Txnrd1 | Thioredoxin reductase | delivers reducing equivalents to Thioredoxin |
| Txn1 | Thioredoxin-like 32 kD | redox balance, reduces dissulphide bridges in proteins |
| Laptm4a | Lysosomal-associated protein transmembrane 4A (MTP) | import of small molecules into lysosome |
| Rcn | Reticulocalbin | ER protein, Ca + 2 binding, overexpressed in tumor cell lines |
| Supl15h | Suppressor of Lec15 homolog | ER synthesis of dolichol phosphate-mannose, precursor to GPI anchors and N-glycosylation |
| Pla2g6 | Phospholipase A2, group VI | hydrolysis of phospholipids |
| Acadm | Acetyl-Coenzyme A dehydrogenase, medium chain | fatty acid beta-oxidation |
| Suclg2 | Succinate-Coenzyme A ligase, GDP-forming, beta subunit | regulatory subunit, Krebs cycle |
| Pex7 | Peroxisome biogenesis factor 7 | Peroxisomal protein import receptor |
| Gcat | Glycine C-acetyltransferase (KBL) | conversion of threonine to glycine |
| Tjp1 | Tight junction protein 1 | component of tight junctions, interacts with cadherins in cells lacking tight junctions |

Embodiments of the invention also include methods for treating a variety of diseases using a reprogrammed cell produced according to the methods disclosed herein. The skilled artisan would appreciate, based upon the disclosure provided herein, the value and potential of regenerative medicine in treating a wide plethora of diseases including, but not limited to, heart disease, diabetes, skin diseases and skin grafts, spinal cord injuries, Parkinson's disease, multiple sclerosis, Alzheimer's disease, and the like. The invention encompasses methods for administering reprogrammed cells to an animal, including humans, in order to treat diseases where the introduction of new, undamaged cells will provide some form of therapeutic relief.

The skilled artisan will readily understand that reprogrammed cells can be administered to an animal as a re-differentiated cell, for example, a neuron, and will be useful in replacing diseased or damaged neurons in the animal. Additionally, a reprogrammed cell can be administered to the animal and upon receiving signals and cues from the surrounding milieu, can re-differentiate into a desired cell type dictated by the neighboring cellular milieu. Alternatively, the cell can be re-differentiated in vitro and the differentiated cell can be administered to a mammal in need there of.

The reprogrammed cells can be prepared for grafting to ensure long term survival in the in vivo environment. For example, cells can be propagated in a suitable culture medium, such as progenitor medium, for growth and maintenance of the cells and allowed to grow to confluence. The cells are loosened from the culture substrate using, for example, a buffered solution such as phosphate buffered saline (PBS) containing 0.05% trypsin supplemented with 1 mg/ml of glucose; 0.1 mg/ml of MgCl.sub.2, 0.1 mg/ml CaCl.sub.2 (complete PBS) plus 5% serum to inactivate trypsin. The cells can be washed with PBS using centrifugation and are then resuspended in the complete PBS without trypsin and at a selected density for injection.

Formulations of a pharmaceutical composition suitable for peritoneal administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for peritoneal administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The invention also encompasses grafting reprogrammed cells in combination with other therapeutic procedures to treat disease or trauma in the body, including the CNS, PNS, skin, liver, kidney, heart, pancreas, and the like. Thus, reprogrammed cells of the invention may be co-grafted with other cells, both genetically modified and non-genetically modified cells which exert beneficial effects on the patient, such as chromaffin cells from the adrenal gland, fetal brain tissue cells and placental cells. Therefore the methods disclosed herein can be combined with other therapeutic procedures as would be understood by one skilled in the art once armed with the teachings provided herein.

The reprogrammed cells of this invention can be transplanted "naked" into patients using techniques known in the art such as those described in U.S. Pat. Nos. 5,082,670 and 5,618,531, each incorporated herein by reference, or into any other suitable site in the body.

The reprogrammed cells can be transplanted as a mixture/solution comprising of single cells or a solution comprising a suspension of a cell aggregate. Such aggregate can be approximately 10-500 micrometers in diameter, and, more preferably, about 40-50 micrometers in diameter. A reprogrammed cell aggregate can comprise about 5-100, more preferably, about 5-20, cells per sphere. The density of transplanted cells can range from about 10,000 to 1,000,000 cells per microliter, more preferably, from about 25,000 to 500,000 cells per microliter.

Transplantation of the reprogrammed cell of the present invention can be accomplished using techniques well known in the art as well those developed in the future. The present invention comprises a method for transplanting, grafting, infusing, or otherwise introducing reprogrammed cells into an animal, preferably, a human.

The reprogrammed cells also may be encapsulated and used to deliver biologically active molecules, according to known encapsulation technologies, including microencapsulation (see, e.g., U.S. Pat. Nos. 4,352,883; 4,353,888; and 5,084,350, herein incorporated by reference), or macroencapsulation (see, e.g., U.S. Pat. Nos. 5,284,761; 5,158,881; 4,976,859; and 4,968,733; and International Publication Nos. WO 92/19195; WO 95/05452, all of which are incorporated herein by reference). For macroencapsulation, cell number in the devices can be varied; preferably, each device contains between $10^3$-$10^9$ cells, most preferably, about $10^5$ to $10^7$ cells. Several macroencapsulation devices may be implanted in the patient. Methods for the macroencapsulation and implantation of cells are well known in the art and are described in, for example, U.S. Pat. No. 6,498,018.

Reprogrammed cells of the present invention can also be used to express a foreign protein or molecule for a therapeutic purpose or for a method of tracking their integration and differentiation in a patient's tissue. Thus, the invention encompasses expression vectors and methods for the introduction of exogenous DNA into reprogrammed cells with concomitant expression of the exogenous DNA in the reprogrammed cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Embodiments of the invention also relate to a composition comprising a cell that has been produced by the methods of the invention. In another embodiment, the invention relates to a composition comprising a cell that has been reprogrammed by inhibiting the expression of at least one gene that codes for a protein involved in transcriptional repression. In yet another embodiment, the invention relates to a composition comprising a cell that has been reprogrammed by inducing the expression of at least one gene that contributes to a cell being pluripotent or multipotent.

Embodiments of the invention also relate to a reprogrammed cell that has been produced by contacting a cell with at least one shRNA or shRNAmir directed toward at least one gene involved in transcription repression.

Embodiments of the invention also relate to kits for preparing the methods and compositions of the invention. The kit can be used for, among other things, producing a reprogramming a cell and generating ES-like and stem cell-like cells, inducing the expression of a gene that contributes to a cell being pluripotent or multipotent, and inhibiting the expression of a gene that codes for a protein involved in transcriptional repression. The kit may comprise at least one shRNA or shRNAmir directed toward a gene that codes for a protein involved in transcriptional repression. The kit may comprise multiple shRNA or shRNAmir sequences or constructs. shRNA or shRNAmir constructs can be provide in a single container or in multiple containers.

The kit may also comprise reagents necessary to determine if the cell has been reprogrammed including but not limited to reagents to test for the induction of a gene that contributes to a cell being pluripotent or multipotent, reagents to test for inhibition of a gene that codes for a protein involved in transcriptional repression, and regents to test for remodeling of the chromatin structure.

The kit may also comprise regents that can be used to differentiate the reprogrammed cell into a particular lineage or multiple lineages including but not limited to a neuron, an osteoblast, a muscle cell, an epithelial cell, and hepatic cell.

The kit may also contain an instructional material, which describes the use of the components provided in the kit. As used herein, an "instructional material" includes a publication, a recording, a diagram, or any other medium of expression that can be used to communicate the usefulness of the methods of the invention in the kit for, among other things, effecting the reprogramming of a differentiated cell. Optionally, or alternately, the instructional material may describe one or more methods of re- and/or trans-differentiating the cells of the invention. The instructional material of the kit of the invention may, for example, be affixed to a container that contains the shRNA or shRNAmir, or component thereof, of the invention. Alternatively, the instructional material may be shipped separately from the container with the intention that the instructional material and the shRNA or shRNAmir, or component thereof, be used cooperatively by the recipient.

The invention is now described with reference to the following Examples. These Examples are provided for the purpose of illustration only and the invention should in no way be construed as being limited to these Examples, but rather should be construed to encompass any and all variations that become evident as a result of the teaching provided herein. All references including but not limited to U.S. patents, allowed U.S. patent applications, or published U.S. patent applications are incorporated within this specification by reference in their entirety.

EXAMPLES

The following examples are illustrative only and are not intended to limit the scope of the invention as defined by the claims.

Example 1

SMARTvector shRNA-GFP-lentivirus for silencing epigenetic regulatory components that contribute to DNA methylation, histone deacetylation, and histone methylation (see Table I) will be introduced into human primary and BJ fibroblast cultures. However, it should be understood that any regulatory component can be targeted using the methods of the invention. Single and synergistic effects of major epigenetic regulatory components will be tested by introducing shRNAs alone and in combinations including but not limited to 2, 3, 4, and 5. Following puromycin-based selection, cells constitutively expressing target shRNA will be harvested to confirm target gene silencing with quantitative real time RT-PCR Methods Cell culture. Human primary fibroblasts (passage 1) and human BJ fibroblasts will be purchased from Cell Applications, Inc. (San Diego, Calif.) and American Type Culture Collection (Manassas, Va.), respectively, and will be maintained at 37° C. in 95% humidity and 5% $CO_2$ in Dulbecco's modified eagle medium (DMEM, Hyclone) containing 10% fetal bovine serum (FBS, Hyclone) and 0.5% penicillin and streptomycin. Cells will be grown, trypsinized and counted, and then will be diluted in the above standard growth media to achieve appropriate plating density prior to introduction of shRNA.

shRNA lentivirus preparation and infection. High tittered SMARTvector shRNA lentivirus ($>10^8$ Transfection Unit/ml) for inactivation of components outlined in Table 1 will be obtained from Dharmacon (Thermo Fisher Scientific). A highly functional long-term gene silencing technology will be utilized from Dharmacon, which is designed for green fluorescence protein (turboGFP™) visualization and puromycin selection as described. The day prior to shRNA lentiviral infection, human fibroblasts will be seeded at a density of $2 \times 10^5$ cells/ml. The next day, the medium will be replaced with pre-warmed medium containing 3 ug/ml polybrene (Sigma) and SMARTvector shRNA lentivirus (25 MOI). Eighteen hours after infection, the medium will be replaced with a new medium, and cells will be assessed for TurboGFP expression by fluorescence microscopy to measure infection efficiency. Three days after infection, puromycin selection will be started by adding puromycin to the culture medium. Selected cells will be harvested to confirm target gene silencing by measuring gene expression levels using quantitative real time RT-PCR.

Quantitative RT-PCR. Expression of shRNA-targeted genes will be quantified by real-time RT-PCR. Briefly, total RNA will be prepared from cultures using Trizol Reagent (Life Technology) and RNeasy Mini kit (Qiagen) with DNase I digestion according to manufacturer's protocol. Total RNA (1 µg) from each sample will be subjected to oligo(dT)-primed reverse transcription (Invitrogen). Real-time PCR reactions will be performed with PCR master mix on a 7300 real-time PCR system (Applied Biosystem). For each sample, 1 µl of diluted cDNA (1:10) will be added as template in PCR reactions. Expression levels will be compared to those in untreated control cells relative to cyclophilin.

shRNA sequences and constructs that inhibit the expression of components in repression complexes will be identified. Various combinations of shRNA sequences and constructs can be tested and optimized using the methods described above. In addition, an shRNAmir sequences and constructs can be used. shRNA libraries and shRNAmir libraries can be used to screen for sequences that inhibit the expression of components in repression complexes.

Example 2

Pluripotency genes are transcriptionally-silenced in somatic cells by repressive epigenetic regulatory components including but not limited to proteins that contribute to DNA methylation, histone deacetylation, and histone methylation. Inhibition of these components by shRNA to induce DNA demethylation, histone acetylation, and histone demethylation may alter chromatin structure and enable transcription of pluripotency genes.

Epigenetic repressive complex targets, such as those identified in Example 1, will be analyzed for chromatin modifications. In addition, human somatic cells that constitutively express target shRNA and exhibit significant target gene expression knockdown or silencing will be analyzed for up-regulation of pluripotency genes.

Global and pluripotency transcript-specific DNA demethylation, histone acetylation, and/or histone demethylation will be confirmed in comparison to untreated control cells using methods outlined below. In addition, up regulation of expression for the pluripotency genes, Oct4, Nanog, and Sox2 (and other stemness-related genes) will be confirmed in comparison to untreated control cells and federally-approved human embryonic stem cells using quantitative real time RT-PCR.

Quantification of global DNA methylation, histone acetylation, and histone methylation. The levels of global DNA methylation, histone acetylation, and histone methylation will be quantified by Methylamp™ Global DNA Methylation Quantification, EpiQuick™ Global Histone Acetylation, and EpiQuick™ Global Histone Methylation Assay Kits from Epigentek (Brooklyn, N.Y.), respectively. In brief, to measure levels of 5-methyl cytosine, genomic DNA (200 ng) from cell cultures will be immobilized on the assay wells by incubating at 37° C. for 2 hrs followed by incubating at 60° C. for 30 min, then blocked by adding blocking buffer. The amount of DNA methylation will be measured by OD intensity from ELISA based reaction using high affinity methylcytone antibody and HRP-conjugated secondary antibody as per manufacturer's protocol.

To measure levels of global histone acetylation, extracted histone will be stably spotted on the assay wells following the manufacturer's protocol. After incubation with antibodies for acetylated histone H3 or H4, the amount of acetylated histone will be quantified through HRP-conjugated secondary antibody-color development on an ELISA reader (BioRad, Hercules, Calif.).

To measure global histone H3-K27 methylation levels, extracted histone proteins will be stably spotted on the assay strip wells following the manufacturer's protocol. After incubation with antibodies specific for methylated H3-K27, the amount of methylated H3-K27 will be quantified through HRP conjugated secondary antibody color development on an ELISA reader (BioRad, Hercules, Calif.).

Bisulfite sequencing analysis of transcript-specific methylation. Methylation of pluripotent gene promoters will be analyzed by bisulfite sequencing. Briefly, DNA will be purified by phenolchloroform-isoamylalcohol extraction. Bisulfite conversion will be performed using the EZ DNA Methylation kit following the manufacturer's protocol (Zymo Research); conversion rates of all cytosines in non-CpG dinucleotides to uracils will be 100%. Converted DNA will be amplified by PCR using primers for human Oct3/4, Nanog, and SOX2. PCR products will be cloned into *E. coli* by TOPO TA cloning kit (Invitrogen. Carlsbad, Calif.). Ten clones of each sample will be verified by sequencing with SP6 and T7 primers. Global methylation percentages for each promoter of interest and numbers of methylated cytosines for a given CpG will be compared between cell populations using paired t-tests.

$Q^2$ChIP analysis of histone modifications. Chromatin immunoprecipitation will be carried out essentially as described by Dahl and Collas (Stem Cells: 25(4):1037-46, 2007). $Q^2$ChIP will be used to monitor changes in histone H3 modifications on the 5' regulatory region of pluripotent genes. Briefly, to prepare antibody-bead complexes, paramagnetic beads (Dynabeads protein A; Dynal Biotech, Oslo, Norway) will be washed in radioimmunoprecipitation assay (RIPA) buffer, then will be resuspended in RIPA buffer. Beads will be added to RIPA buffer containing 2.4 µg of primary antibody, then will be incubated on a rotator for 2 h at 4° C. For DNA-protein cross-linking, 20 mM of the histone deacetylase inhibitor sodium butyrate will be added to cells immediately before harvesting (and to all solutions thereafter). Cells will be fixed in suspension with 1% formaldehyde at 1-2×10$^6$ cells/ml. Cross-linked cells will be washed in PBS/20 mM butyrate and lysed in lysis buffer containing butyrate. Aliquots will be sonicated to generate chromatin fragments of 500 base pairs. The lysate will be sedimented, the supernatant will be collected, and chromatin concentration will be determined by A$_{260}$ from a diluted aliquot. Chromatin in RIPA buffer/butyrate will be transferred to a tube containing antibody-bead complexes (see above), and the sample will be incubated as above. Immune complexes will be washed in RIPA buffer then TE buffer. The ChIP material will be incubated in elution buffer containing 1% SDS and 50 µg/ml proteinase K, and will be incubated for 2 h at 68° C. on a Thermomixer at 1300 rpm. Elution buffer will be recovered, the ChIP material will be re-extracted, and both supernatants pooled. DNA will be extracted once with phenol-chloroform isoamyl alcohol, once with chloroform isoamyl alcohol, then ethanol precipitated. Immunoprecipitated DNA will be analyzed in triplicates by real-time PCR starting with 5 µl of DNA.

Quantitative RT-PCR for pluripotency gene expression analysis. Expression of pluripotent genes, such as Oct4, Nanog, SOX2, glycine N-methyltransferase (Gnmt), REX-1 (also known as Zfp-42), Integrin α-6, Rox-1, LIF-R, TDGF1 (CRIPTO), SALL4 (sal-like 4), LECT1, BUB1, Klf4 and Klf5 will be quantified by real-time RT-PCR essentially as described in Aim 1. Expression levels will be compared to those in untreated control cells and federally-approved human embryonic stem cells (ATCC) relative to cyclophilin.

Taqman Low Density Array analysis (TLDA). A TLDA containing embryonic stem cell and developmental genes will be used for quantitative real time RT-PCR to quantify relative expression levels for pluripotent and other stemness-related genes. The Applied Biosystems Human Embryonic Taqman Low Density Array (Human Embryonic TLDA) containing 90 embryonic stem cell and developmental genes and 6 endogenous control genes will be used for quantitative real time RT-PCR. Briefly, following reverse-transcription of RNA using the ABI High Capacity cDNA Reverse Transcription Kit (Applied Biosystems, Foster City, Calif.), 150 ng sample cDNA in 50 µl nuclease-free water and 50 µl ABI Universal Taqman 2×PCR Master Mix will be pipetted into each port of the Human Embryonic TLDA microfluidic card, and will be analyzed on the ABI 7900HT Fast Real Time PCR System (Applied Biosystems, Foster City, Calif.). The $^{\Delta\Delta}$CT method will be used to calculate relative quantities (fold change) in gene expression levels in treated cells compared to untreated control cells and federally-approved human embryonic stem cells.

Western blotting. Translation of pluripotency gene expression will be confirmed by Western blot for protein expression. Briefly, total cell lysates will be prepared by adding RIPA buffer supplemented with protease inhibitor cocktails (Sigma, St. Louis, Mo.) into cell culture. MEL-1 hES cell lysates from Abcam (Cambridge, Mass.) will be used as a positive control. Cell lysates (50 µg) will be separated by electrophoresis and transferred to PVDF membrane (Millipore, Billerica, Mass.). The blot will be blocked with blocking buffer (Licor Bioscience, Lincoln, Nebr.) for 1 hr, rinsed and incubated with primary antibody at 4° C. overnight. Bands will be visualized using the Odyssey imaging system (Licor Bioscience, Lincoln, Nebr.) with fluorescent labeled secondary antibody, such as IRDye800™ or Cy5.5 (Rockland, Philadelphia, Pa.) according to the manufacturers protocol. Antibodies for western blotting will be obtained from several sources: Oct3/4 (Santa Cruz Biotechnology, Santa Cruz, Calif.); Sox2 (Chemicon, Temecula, Calif.); β-actin, a loading control (BD Biosciences, San Jose, Calif.); Alexa conjugated anti mouse and goat IgG (Molecular Probes, Invitrogen, Carlsbad, Calif.); IRDye800™ conjugated anti rabbit IgG (Rockland, Philadelphia, Pa.); and Nanog (R&D systems, Minneapolis, Minn.).

Example 3

Repressive epigenetic targets will be analyzed by assessing the ability to form colony units under human ES cell culture conditions and differentiation capacity, in vitro and in vivo, in puromycin-selected human somatic cells constitutively expressing target shRNA, which exhibit up regulation of pluripotency genes (ie., Oct4, Nanog, Sox2, and/or other stemness-related genes). To accomplish this, cells will be cultured under human (ES) cell culture conditions and embryonic stem cell-like colony formation will be quantified. Colonies then will be harvested for in vitro directed differentiation into multiple lineages using cocktails outlined below. In addition, colony cells will be injected into immune-deficient Nude mice to assess capacity for teratoma formation, in vivo. Phenotypes assessed as described will be compared to untreated control cells and federally-approved human embryonic stem cells.

Human ES cell culture for colony unit formation. Puromycin-selected somatic cells that constitutively express shRNA, which is directed toward a component of a repression complex, will be established and maintained in human ES cell medium (hESC Medium; Invitrogen, Carlsbad, Calif.) containing 4 ng/ml bFGF (Invitrogen, Carlsbad, Calif.). Mouse embryonic fibroblasts (MEF, CF1 strain) will be purchased from ATCC (Manassas, Va.) and mitotically inactivated by treatment with 10 µg/ml mitomycin C (Roche, Basel, Switzerland). Immediately before plating these cells, MEFs will be rinsed twice with PBS. Cells will be fed every day until ready to passage, which will be determined by the size and quantity of colonies. For passing the cells, cells will be washed twice with PBS and will be incubated with filter-sterilized 1 mg/ml collagenase IV in DMEM/F12 for 10 min. When colonies begin to detach, they will be collected and washed with appropriate volume of culture medium. Cells will be passaged at a ratio of between 1:3 and 1:6 every four to seven days.

Directed Differentiation, In Vitro:

1. Neuronal/Glial differentiation: To induce neuronal differentiation, the treated cells will be exposed to a cocktail of induction agents as known in the art. Briefly, dedifferentiated cells from passages, for example passages 2-5, will be grown to 80% confluence and neuronal induction media (NIM) will be added after a quick wash with PBS. NIM will be comprised of alpha-MEM without serum, with added butylated hydroxianisole (200 µM), KCL (5 nM) valproic acid (2 mM), forskolin (10 µM), hydrocortisone (1 µM) and insulin (5 µg/ml). Experiments will be performed within 5 h to 15 days following exposure to neuronal induction media.

Neuronal Differentiation Assays:

A. Viability assay: To determine the viability of dedifferentiated cells after exposure to neuronal induction media, a dye exclusion assay will be used. At daily time points from 1-5 days after induction, Hoechst dye (200 μg/ml) (Intergen; Purchase, N.Y.) will be added to the cells in culture. The viability of cells grown in control media will be determined for comparison to neuronally induced cells. Viability will be determined by counting live cells using phase microscopy in non-overlapping fields, for example three non-overlapping fields. Differences between control and induced cells will be compared using a Student's t-test. This assay will be standard for all differentiation induction treatments.

B. NMDA-induced excitotoxicity assay: To measure the response of demethylated cells to the glutamate antagonist N-methyl-D-aspartic acid (NMDA), we will quantify the effect of NMDA on cell viability. Triplicate cultures of cells will be grown in control or induction media for 24 hours. The cells will be exposed to 500-1000 μM NMDA for 30 minutes. As a control, one group of cells will be exposed to both 1000 μM NMDA and the NMDA antagonist, Dizocilpine (MK-801) (10 μM) for 30 minutes. Cell viability will be examined after NMDA exposure by incubating cells with Hoechst dye and counting live cells by phase microscopy in non-overlapping fields, for example three non-overlapping fields, with values expressed as ±SD.

C. Immunocytochemistry: To determine phenotype, cells will be grown under control or induction conditions on chambered slides (LabTek, Napersville, Ill.). At various time points after neuronal induction (5 h to 15 days), cells will be fixed with 4% paraformaldehyde. After fixation, cells will be incubated with specific monoclonal antibodies directed against the following markers of neural and glial cells: nestin, GFAP, S-100, NeuN, MAP2, β-tubulin III, tau, NMDAR-1, g-aminobutyric acid (GABA), 5HTP, TH, DDC, GAP-43, synapsin I, pan α-1 voltage gated calcium channel (all obtained from Chemicon, Inc.; Temecula, Calif.) and NMDAR-2 (Santa Cruz Biotechnology). The ABC amplification kit (Vector Laboratories, Burlingame, Calif. and Santa Cruz Biotechnology) will be used with all antibodies. To identify co-expression of NeuN and GFAP, or MAP2 and tau, cells will be incubated with each antibody sequentially. An avidin/biotin blocking kit with Texas Red and fluoroscein avidins (Vector Laboratories and Santa Cruz biotechnology) will be used to label the antibodies. At time points from 1-15 days after neuronal induction, the morphologies will be examined and photographed using bright field and phase-contrast microscopy. Two independent investigators will count the percentage of positive cells per field in random, non-overlapping visual fields, using cultures from a minimum of three different experiments.

Western blot: To confirm protein expression following neuronal induction, cells grown under control and experimental conditions will be harvested 1-15 days after neuronal induction and subjected to Western blot analysis following essentially the same procedures as described above. Murine brain extract will serve as a positive control and actin will serve as an internal protein control.

Real time TaqMan RT-PCR: In addition, neuronal associated markers such as nestin, intermediate filament M and Neu N, S-100, MAP2, β-III tubulin and glutamate receptor subunits NR-1 and NR-2 will be screened by real time Taqman PCR essentially as described.

2. Osteogenic differentiation: To determine the capacity of demethylated cells to differentiate into Osteoblast-like cells, confluent cells (control and experimental) will be grown for 20 days in DMEM-F12 supplemented with 10% FBS, 200 μM ascorbic acid 2-phosphate, 100 nM dexamethasone, 7 mM β-glycerophosphate and 1 nM 1α,25-dihydroxyvitamin D3. After induction, cells will begin to show evidence of mineralizing their extracellular matrix in vitro and express genes and proteins associated with the phenotype. Markers indicative of osteogenic differentiation, including but not limited to alpha 1(I)-procollagen, osteocalcin, osteopontin, bone sialoprotein, ALP and cbfa1, will be assessed by real time TaqMan PCR and immunochemistry using methods essentially as already described. In addition, cells will be fixed in 10% buffered formalin and alkaline phosphatase histochemistry will be performed to detect osteoblasts using the Sigma diagnostic kit 85 according to manufacturers protocol (Sigma, St. Louis, Mo.).

3. Myogenic differentiation: Differentiation of control and experimental cells into muscle-like lineage will be induced with DMEM-F12 supplemented with 10% horse serum. Expression of muscle markers MyoD, myogenin, TroponinT, Titin and myosin will be assessed using methods essentially as described.

4. Hepatogenic differentiation: Hepatogenic differentiation will be carried out using a 2-step protocol with sequential addition of growth factors and cytokines as described by Talens-Visconti et al. (World J Gastroenterol., Sep. 28; 12(36):5834-45, 2006). Briefly, prior to induction of hepatogenic differentiation, cells (85% confluent) will be cultured in serum deprived DMEM supplemented with 20 ng/ml EGF and 10 ng/ml bFGF to stop cell proliferation. Two days later, the 2 step differentiation protocol will be performed as follows: Step-1 differentiation medium consisting of DMEM supplemented with 20 ng/ml HGF, 10 ng/ml bFGF, and 4.9 μM/L nicotinamide for 7 days, followed by step-2 differentiation medium, consisting of DMEM supplemented with 20 ng/ml Oncostatin M (OMS), 1 μM/L dexamethasone, and 10 μL/ml insulin/transferin/selenium (ITS, Sigma, St, Louis Mo.))+premix (final concentration: 100 μM/L insulin, 6.25 μg/ml transferrin, 3.6 μM/L selenious acid, 1.25 mg/ml BSA and 190 μM/L linoleic acid) to achieve cell maturation for up to 21 days. Media will be changed twice weekly and hepatic differentiation will be assessed by RT-PCR for liver-associated genes (C/EBP, HNF4, CYP3A4) as described.

In vivo teratoma formation. Colony cells that will be established from Puromycin-selected human somatic cells that constitutively express target shRNA, untreated control cells, and federally-approved human ES cells will be re-suspended in 250 μl sterile BD Matrigel (BD Biosciences, San Jose, Calif.) at an approximate concentration of 10 million cells/ml and injected into female 6-week-old immune deficient athymic nude mice (Charles River; 25/group); an additional subset of mice will be injected with Matrigel alone to serve as a vehicle control group. While under isoflurane anesthesia, cell suspensions will be injected into the mice by forming a subcutaneous pocket by swaying the needlepoint right and left after a routine subcutaneous insertion, and the Matrigel cell suspension then will be injected into this pocket as per manufacturer's recommendations. Injection sites will be routinely examined, and 5 mice from each group will be euthanized at 2, 4, 6, 8, and 12 weeks after injection. Following euthanasia, injection sites and any apparent masses will be dissected and fixed for histological examination to confirm teratomas containing multiple differentiated cells types and lineage specific tissues as evidenced by lineage- and tissue-specific staining.

The cells in culture may represent pluripotent cells including but not limited to 1-5%, 5-10%, 10-20%, 20-30%, 30-40%, 40-50%, 50-60%, 60-70%, 70-80%, 80-90%, 90-95%, and 95-100% pluripotent cells. The cells in culture may represent multipotent cells including but not limited to 1-5%, 5-10%, 10-20%, 20-30%, 30-40%, 40-50%, 50-60%, 60-70%, 70-80%, 80-90%, 90-95%, and 95-100% multipotent cells. The cells in culture may represent a variety of cell populations, including but not limited to a pluripotent cell, a multipotent cell, a cell capable of differentiating into 1, 2, 3, 4, 5, 6, 7, 8, 9, 10, 11-20, 21-30, and greater than 30 lineages. Protocols can be used to enrich for cells whose potential is restored using FACS to separate cells based on the expression of cell surface markers associated with pluri- or multipotent.

In some embodiments, the methods herein can be used to identify repressive epigenetic targets. In yet another embodiment, the inhibition of repressive epigenetic components, for example proteins, can induce epigenetic changes including but not limited to DNA demethylation, histone acetylation, and/or histone demethylation, and lead to the identification of any and all lineages into which cells are capable of redifferentiation. In yet another embodiment, the methods, as described herein, can lead to a modification of chromatin structure, and restore differentiation potential to a somatic cell.

Example 4

An shRNA construct directed toward DNMT1 was investigated to determine the effects on the expression of pluripotent genes. In this experiment, the shRNA was directed to a DNA methyltransferase, however, any shRNA construct can be used that increase the expression of at least one pluripotent gene.

Methods

Cell culture. Adult human dermal fibroblasts were purchased from Cell Applications (San Diego, Calif.), and were maintained at 37° C. in 95% humidity and 5% $CO_2$ in Fibroblast growth medium (Cell Applications, San Diego, Calif.).

Lentiviral Infection. Adult human dermal fibroblasts were infected with shRNA lentivirus directed to DNMT1. The lentiviral construct contained the Turbo GFP reporter. The shRNA construct was obtained from Dharmacon and had the following sequence:

SEQ ID NO. 1: GTCTACCAGATCTTCGATA

The human dermal fibroblasts were infected with the shRNA following the manufacturer's instructions. HDF were cultured with an without puromycin selection and hES culture conditions (mTeSR Medium, Stem Cell Technology, Vancouver, BC, Canada) on matrigel (BD Biosciences, San Jose Calif.).

Quantitative RT-PCR. Expression of Oct-4 and DNMT1 were determined by real-time RT-PCR. Briefly, total RNA was prepared from cultures using Trizol Reagent (Life Technologies, Gaithersburg, Md.) and RNeasy Mini kit (Qiagen; Valencia, Calif.) with DNase I digestion according to manufacturer's protocol. Total RNA (1 µg) from each sample was subjected to oligo(dT)-primed reverse transcription (Invitrogen; Carlsbad, Calif.). Real-time PCR reactions will be performed with PCR master mix on a 7300 real-time PCR system (Applied Biosystems; Foster City, Calif.). For each sample, 1 µl of diluted cDNA (1:10) will be added as template in PCR reactions. The expression level of Oct-4 and DNMT1 was normalized to glyceraldehyde 3-phosphate-dehydrogenase (GAPD).

Immunohistochemistry. For immunohistochemistry, target shRNA-infected and control cells were grown on chambered slides (LabTek, Napersville, Ill.). Cells were then be fixed with 4% paraformaldehyde, and incubated with specific antibodies directed against pluripotency markers (Oct3/4, Nanog, Sox2 and SSEA4 from Abcam, Cambridge, Mass.) following the manufacturer's protocol. Cells were observed on microscope with green fluorescence light (Nikon Corporation, Tokyo, Japan).

Results

As shown in FIG. 1A, Oct-4 expression was increased in HDFs that were infected with DNMT1 shRNA. Conversely, DNMT1 expression was reduced in HDFs that were infected with DNMT1 shRNA. The increase in expression of Oct-4 appeared to peak at 5 days post transfection.

Figure 1B:
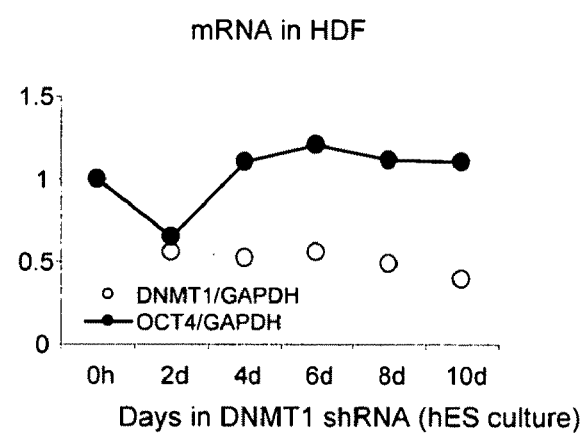
FIG. 1B is a graph reporting the increase in expression of Oct-4 and decrease in expression of DNMT1 in cells infected with DNMT1 shRNA and cultured in hES medium.
Figure 2:
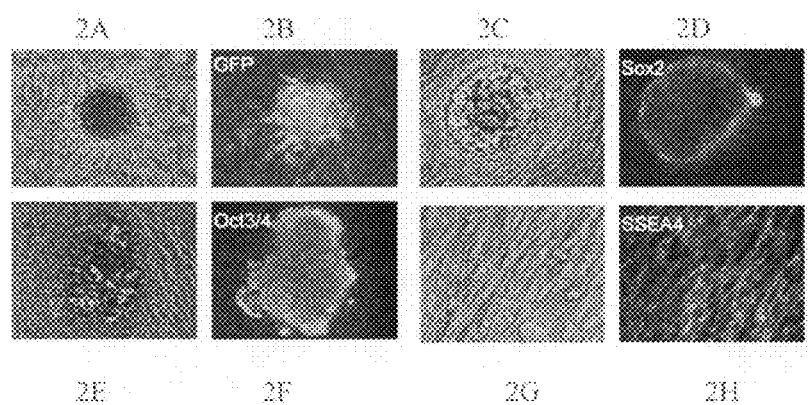
FIG. 2A is a photograph of an embryonic-like body formed after shRNA knockdown of DNMT1.
FIG. 2B is a photograph demonstrating GFP localization in cells present within the embryoid-like body shown in FIG. 2A, confirming lentiviral infection.
FIG. 2C is a photograph of an embryonic-like body formed after shRNA knockdown of DNMT1
FIG. 2D is a photograph demonstrating expression of Sox2 protein induced by shRNA knockdown of DNMT1 in the embryonic-like body shown in FIG. 2C.
FIG. 2E is a photograph of an embryonic-like body formed after shRNA knockdown of DNMT1.
FIG. 2F is a photograph demonstrating expression of Oct4 protein induced by shRNA knockdown of DNMT1 in the embryonic-like body shown in FIG. 2E.
FIG. 2G is a photograph of fibroblasts growing in culture.
FIG. 2H is a photograph demonstrating expression of SSEA4 protein induced by shRNA knockdown of DNMT1 in the embryonic-like body shown in FIG. 2G.

FIG. 1B depicts data from HDFs that were infected with DNMT1 shRNA and cultured in the presence of puromycin. Oct-4 expression was increased and was maintained for the time period tested. The expression of DNMT1 was reduced in the presence of DNMT1 shRNA Expression of turboGFP, Oct4, Sox-2 and SSEA4 in colonies was visualized by immunohistochemistry using specific antibodies and green fluorescence microscopy. FIG. 2A is a photograph of an embryonic-like body formed after shRNA knockdown of DNMT1. FIG. 2B is a photograph demonstrating GFP localization in cells present within the embryoid-like body shown in FIG. 2A, confirming lentiviral infection. FIG. 2C is a photograph of an embryonic-like body formed after shRNA knockdown of DNMT1. FIG. 2D is a photograph demonstrating expression of Sox2 protein induced by shRNA knockdown of DNMT1 in the embryonic-like body shown in FIG. 2C. FIG. 2E is a photograph of an embryonic-like body formed after shRNA knockdown of DNMT1. FIG. 2F is a photograph demonstrating expression of Oct4 protein induced by shRNA knockdown of DNMT1 in the embryonic-like body shown in FIG. 2E. FIG. 2G is a photograph of fibroblasts growing in culture. FIG. 2H is a photograph demonstrating expression of SSEA4 protein induced by shRNA knockdown of DNMT1 in the embryonic-like body shown in FIG. 2G.

These data demonstrate that DNMT1 mRNA interference using shRNA lentiviral infection can produce embryonic-like bodies that positively stain with oct-4, Sox2 and SSEA4 antibodies. Several colonies were observed from human dermal fibroblasts after DNMT shRNA infection. Green fluorescence protein was utilized as an shRNA expression marker.

Example 5

Methods

Cell culture. Fetal and neonatal human dermal fibroblasts were purchased from Cell Applications (San Diego, Calif.), and were maintained at 37° C. in 95% humidity and 5% $CO_2$ in Fibroblast growth medium (Cell Applications, San Diego, Calif.).

Lentiviral Infection. Adult human dermal fibroblasts were infected with shRNA lentivirus directed to DNMT1. The shRNA construct was obtained from Dharmacon and had the following sequence:

SEQ ID NO. 1: GTCTACCAGATCTTCGATA

The human dermal fibroblasts were infected with the shRNA following the manufacturer's instructions. HDF were cultured with an without puromycin selection and hES culture conditions (mTeSR Medium, Stem Cell Technology, Vancouver, BC, Canada) on matrigel (BD Biosciences, San Jose Calif.).

Quantitative RT-PCR. Expression of Oct-4, DNMT1 and Sox-2 was determined by real-time RT-PCR. Briefly, total RNA was prepared from cultures using Trizol Reagent (Life Technologies, Gaithersburg, Md.) and RNeasy Mini kit (Qiagen; Valencia, Calif.) with DNase I digestion according to manufacturer's protocol. Total RNA (1 µg) from each sample was subjected to oligo(dT)-primed reverse transcription (Invitrogen; Carlsbad, Calif.). Real-time PCR reactions will be performed with PCR master mix on a 7300 real-time PCR system (Applied Biosystems; Foster City, Calif.). For each sample, 1 µl of diluted cDNA (1:10) will be added as template in PCR reactions. The expression level of Oct-4 and DNMT1 was normalized to glyceraldehyde 3-phosphate-dehydrogenase (GAPD).

Results

As shown in FIG. 3A, Oct-4 expression was increased in fetal human dermal fibroblasts (HDFf) infected with DNMT1 shRNA. Expression of Oct-4 peaked at about day 2. Expression of DNMT1 was reduced in cells infected with DNMT1 shRNA. Oct-4 expression was increased in DNMT1 shRNA infected cells grown in the presence of puromycin (FIG. 3B) and in cells grown in puromycin and hES culture (FIG. 3C). Under all culture conditions, expression of DNMT1 was reduced (FIG. 3A-3C).

Initial infection efficiency of shRNA lentivirus into human dermal fibroblasts was around 70-80%. Culturing cells in medium containing puromycin can select only shRNA lentivirus infected cells as the shRNA construct contains a puromycin resistance gene. Culturing in hES cell culture conditions contributes to the efficiency and efficacy of reprogramming cells and restoring differentiation potential to cells.

Figure 4A:
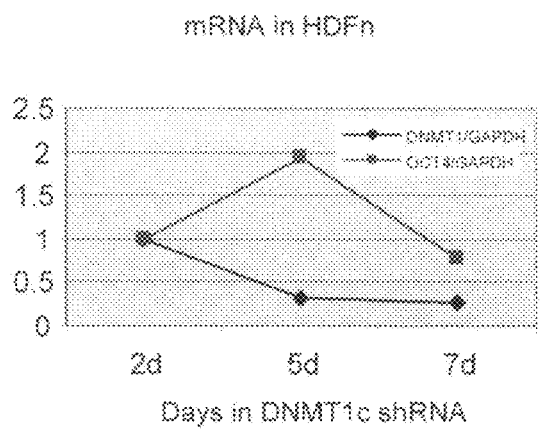
FIG. 4A is a graph reporting the increase in expression of Oct-4 and decrease in expression of DNMT1 in neonatal human dermal fibroblast cells infected with DNMT1 shRNA
Figure 4B:
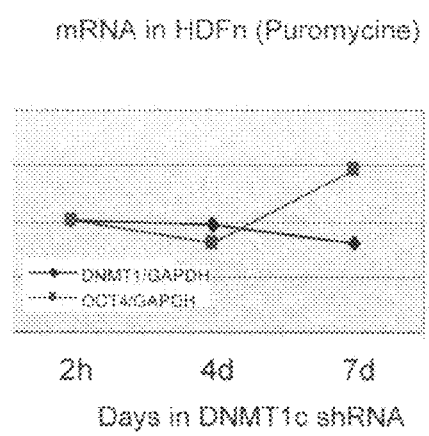
FIG. 4B is a graph reporting the increase in expression of Oct-4 and decrease in expression of DNMT1 in neonatal human dermal fibroblast cells infected with DNMT1 shRNA and cultured in presence of puromycin.
Figure 4C:
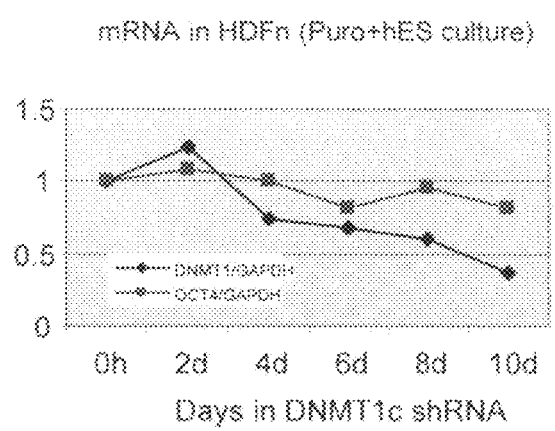
FIG. 4C is a graph reporting the increase in expression of Oct-4 and decrease in expression of DNMT1 in neonatal human dermal fibroblast cells infected with DNMT1 shRNA and cultured in presence of puromycin and hES culture.

Expression of Oct-4 was also increased in other cell types infected with DNMT1 shRNA. For instance, Oct-4 expression was increased in neonatal human dermal fibroblasts (HDFn) infected with DNMT1 shRNA (see FIG. 4A-4C). The increase in expression in Oct-4 varied for the different culture conditions, as demonstrated by the moderate increase in Oct-4 expression in HDFn cells cultured in presence of puromycin and hES culture. Under all culture conditions tested for the infected HDFn cells, DNMT1 expression was reduced.

These results demonstrate that the expression of a pluripotent gene can be increased by using shRNA constructs to interfere with the expression of genes that code for proteins that are involved in silencing pluripotent genes and/or involved in transcriptional repression. An shRNA construct directed toward a DNA methyltransferase increased the expression of a pluripotent gene. This methodology can be used to reprogram a cell and to restore differentiation potential to a cell. Any shRNA construct that interferes with expression of genes that code for regulatory proteins may be used. One of ordinary skill in the art will understand that the methods of this example extend beyond DNMT1 and can be directed toward any regulatory protein or regulatory protein family member.

Example 6 shRNA constructs directed toward genes that code for regulatory proteins were investigated for the ability to increase expression of pluripotent genes. Oct-4 and Nanog were analyzed in the present example. One of ordinary skill in the art will understand that the methods can be used to increase expression of any gene involved in reprogramming and/or restoring differentiation potential to a cell.

Methods:

Cell culture. Adult, fetal and neonatal human dermal fibroblasts were purchased from Cell Applications (San Diego, Calif.), and were maintained at 37° C. in 95% humidity and 5% $CO_2$ in Fibroblast growth medium (Cell Applications, San Diego, Calif.).

Lentiviral Infection. Adult human dermal fibroblasts were infected with shRNA lentivirus directed to either HDAC7a or HDAC11. shRNA constructs were obtained from Dharmacon. The shRNA construct directed toward HDAC7a had the following sequence:

SEQ ID NO. 2: GCTTTCAGGATAGTCGTGA

An shRNA construct with the following sequence was directed against HDAC11:

SEQ ID NO. 3: AGCGAGACTTCATGGACGA

In addition, an shRNA construct with the following sequence was directed against HDAC 11:

SEQ ID. NO. 4: TGGTGGTATACAATGCAGG

The human dermal fibroblasts were infected with the shRNA following the manufacturer's instructions. HDF were cultured with an without puromycin Quantitative RT-PCR. Expression of Oct-3/4 and Nanog was determined by real-time RT-PCR. Briefly, total RNA was prepared from cultures using Trizol Reagent (Life Technologies, Gaithersburg, Md.) and RNeasy Mini kit (Qiagen; Valencia, Calif.) with DNase I digestion according to manufacturer's protocol. Total RNA (1 µg) from each sample was subjected to oligo(dT)-primed reverse transcription (Invitrogen; Carlsbad, Calif.). Real-time PCR reactions will be performed with PCR master mix on a 7300 real-time PCR system (Applied Biosystems; Foster City, Calif.). For each sample, 1 µl of diluted cDNA (1:10) will be added as template in PCR reactions. The expression level of Oct-3/4 and Nanog was normalized to glyceraldehyde 3-phosphate-dehydrogenase (GAPD).

Figure 5A:
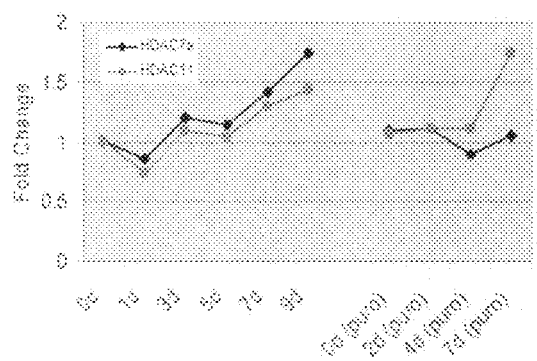
FIG. 5A is a graph reporting an increase in expression of Oct-4 mRNA in adult human dermal fibroblast cells in presence of HDAC7a and HDAC11 shRNA.
Figure 5B:
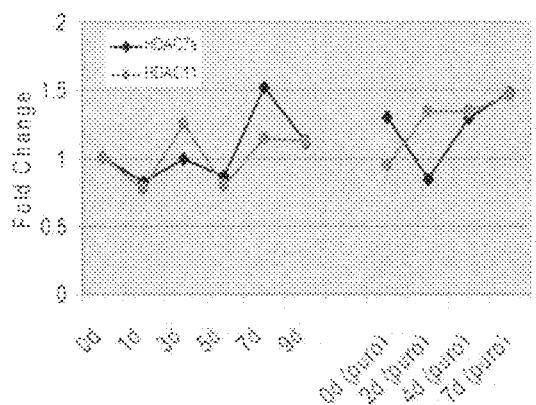
FIG. 5B is a graph reporting an increase in expression of Oct-4 mRNA in neonatal human dermal fibroblast cells in presence of HDAC7a and HDAC11 shRNA.
Figure 5C:
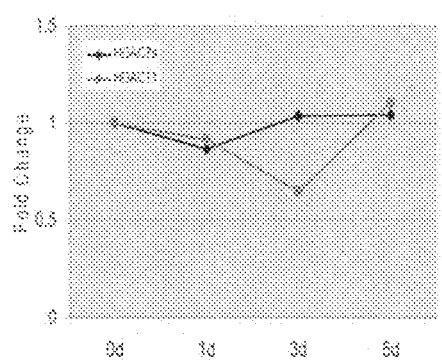
FIG. 5C is a graph reporting an increase in expression of Oct-4 mRNA in fetal human dermal fibroblast cells in presence of HDAC7a and HDAC11 shRNA.

Results shRNA constructs directed toward two different histone deacetylases were investigated. As shown in FIG. 5A, Oct3/4 expression was increased about two-fold in adult human dermal fibroblasts infected with HDAC7 or HDAC11 shRNA. The increase in expression was modest in cells cultured in the presence of puromycin with HDAC7a shRNA. Similar results were seen in neonatal human dermal fibroblasts cultured in the presence and absence of puromycin (FIG. 5B). The increase in expression of Oct-4 was particularly modest in fetal human dermal fibroblasts (FIG. 5C), which may be stem from the fact that fetal human dermal fibroblasts exhibit about four times higher basal expression of Oct-4 than adult and neonatal human dermal fibroblasts.

Figure 6A:
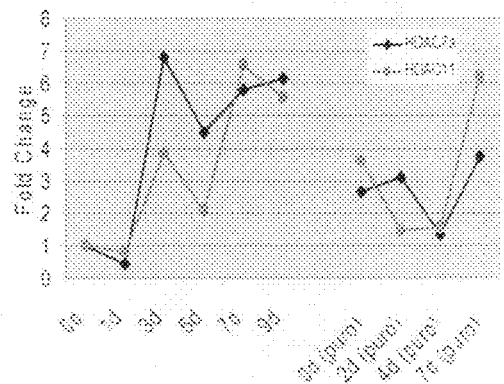
FIG. 6A is a graph reporting an increase in expression of Nanog mRNA in adult human dermal fibroblast cells in presence of HDAC7a and HDAC11 shRNA.
Figure 6B:
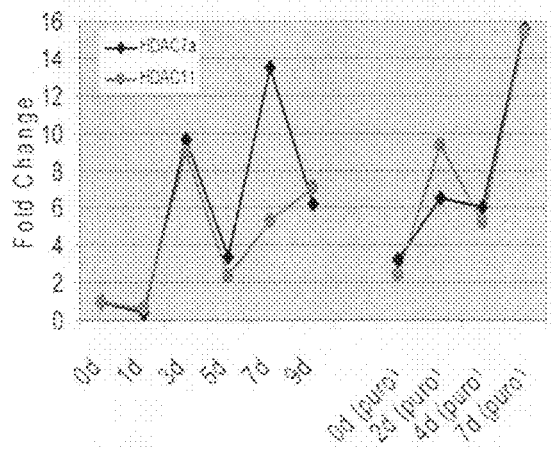
FIG. 6B is a graph reporting an increase in expression of Nanog mRNA in neonatal human dermal fibroblast cells in presence of HDAC7a and HDAC11 shRNA.
Figure 6C:
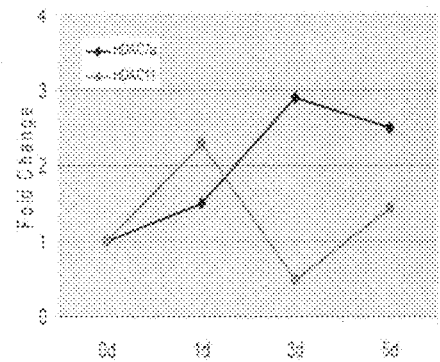
FIG. 6C is a graph reporting an increase in expression of Nanog mRNA in fetal human dermal fibroblast cells in presence of HDAC7a and HDAC11 shRNA.

Nanog expression was increased in adult human dermal fibroblasts infected with either HDAC7a or HDAC11 shRNA (FIG. 6A). The increase in expression was observed with cells cultured in the presence and absence of puromycin. Similar results were observed with neonatal human dermal fibroblasts, cultured in the presence or absence of puromycin (FIG. 6B). The expression of Nanog was increased in fetal human dermal fibroblasts, although not as dramatically as in the other cell types tested. shRNA directed against HDAC7a produced a more robust effect compared to shRNA HDAC11 in fetal human dermal fibroblasts, although both HDAC7a shRNA and HDAC11 shRNA led to increase in Nanog expression.

As evidenced by the data presented herein, shRNA constructs directed toward HDACs result in an increase in the expression of pluripotent genes. Both Oct-3/4 and Nanog were increased in cells infected with shRNA constructs directed toward HDAC7a and HDAC11. These results demonstrate that shRNA constructs directed toward genes that code for regulatory proteins, both positive and negative regulators, can be used to reprogram a cell and restore differentiation potential to a cell.

Example 7

Cells infected with lentivirus shRNA directed to HDAC7, HDAC11 or DNMT1 were stained and visualized for expression of pluripotent genes. Protein expression of Oct-4 and Sox-2 was analyzed in this example, but one of ordinary skill in the art will understand the methods of the invention can be used to increase expression of any gene involved in reprogramming or restoring differentiation potential to a cell.

Methods

Cell culture. Fetal human dermal fibroblasts were purchased from Cell Applications (San Diego, Calif.), and were maintained at 37° C. in 95% humidity and 5% $CO_2$ in Fibroblast growth medium (Cell Applications, San Diego, Calif.).

Lentiviral Infection. Fetal human dermal fibroblasts were infected with one of the following compositions: (1) shRNA lentivirus directed to DNMT1; (2) shRNA lentivirus directed toward HDAC7; (3) shRNA lentivirus directed toward DNMT1 and HDAC7; and (4) shRNA lentivirus directed toward HDAC7a and HDAC11. The shRNA construct was obtained from Dharmacon. The shRNA construct directed toward DNMT1 had the following sequence:

SEQ ID NO. 1: GTCTACCAGATCTTCGATA

The shRNA construct directed toward HDAC7a had the following sequence:

SEQ ID NO. 2: GCTTTCAGGATAGTCGTGA

An shRNA construct with the following sequence was directed against HDAC11:

SEQ ID NO. 3: AGCGAGACTTCATGGACGA

In addition, an shRNA construct with the following sequence was directed against HDAC11:

SEQ ID. NO. 4: TGGTGGTATACAATGCAGG

The human dermal fibroblasts were infected with the shRNA following the manufacturer's instructions. HDF were cultured with an without puromycin selection and hES culture conditions (mTeSR Medium, Stem Cell Technology, Vancouver, BC, Canada) on matrigel (BD Biosciences, San Jose Calif.).

Immunohistochemistry. For immunohistochemistry, target shRNA-infected and control cells were grown on chambered slides (LabTek, Napersville, Ill.). Cells were then fixed with 4% paraformaldehyde, and incubated with a specific antibody directed against pluripotency marker Oct3/4 (Abcam, Cambridge, Mass.) following the manufacturer's protocol. Staining of Oct3/4 was visualized as a red color. The nucleus was visualized with DAPI staining (Vectorshield), which appeared as a blue color.

Results

Figure 7:
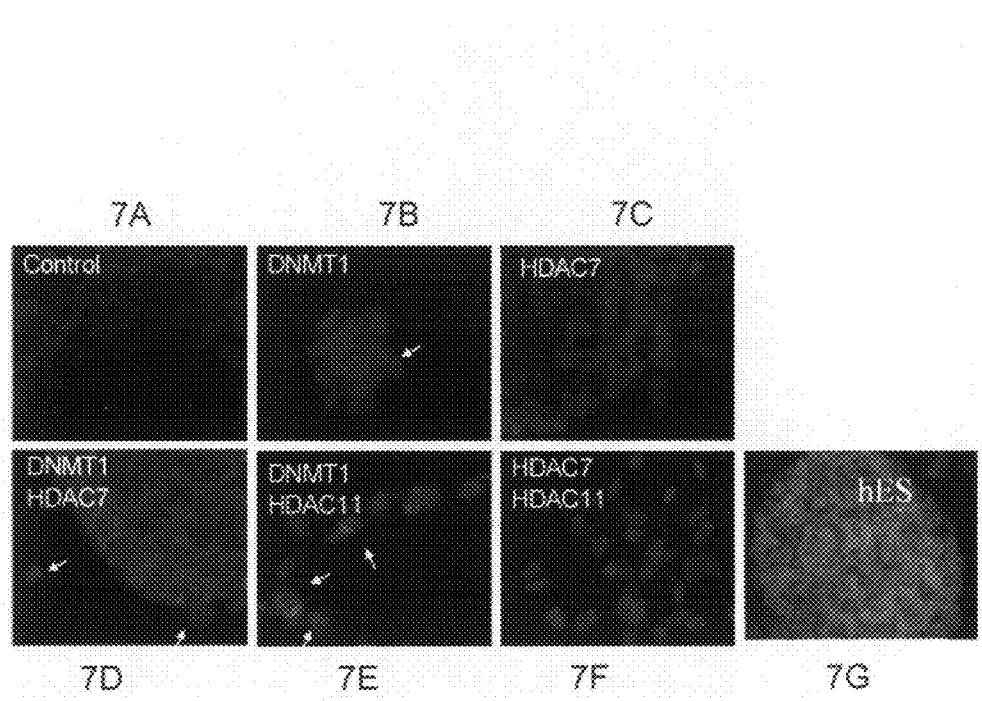
FIG. 7A is a photograph of fetal human dermal fibroblasts.
FIG. 7B is a photograph of fetal human dermal fibroblasts infected with DNMT1 shRNA.
FIG. 7C is a photograph of fetal human dermal fibroblasts infected with HDAC7 shRNA.
FIG. 7D is a photograph of fetal human dermal fibroblasts infected with DNMT1 and HDAC7 shRNA.
FIG. 7E is a photograph of fetal human dermal fibroblasts infected with DNMT1 and HDAC11 shRNA.
FIG. 7F is a photograph of fetal human dermal fibroblasts infected with HDAC11 and HDAC7 shRNA.
FIG. 7G is a photograph of human embryonic stem cells.

Oct-4 protein expression was increased in fetal human dermal fibroblasts (HDFf) by shRNA interference. FIG. 7A is a photograph of HDFf without infection (negative control) and FIG. 7G is a photograph of human embryonic stem cells (positive control). In the negative control cells, little expression of Oct-4 protein was detected. FIG. 7B is a photograph of HDFf cells infected with shRNA directed toward DNMT1. Oct-4 protein expression is clearly increased when cells are exposed to DNMT1 shRNA. HDFf cells infected with HDAC7 shRNA show minimal detection of Oct-4 protein (FIG. 7C). This may be due to the processing of this particular sample.

Cells infected with DNMT1 and HDAC7 shRNA showed a dramatic increase in the expression of Oct-4 protein (FIG. 7D). The cells treated with both DNMT1 and HDAC7 shRNA produced an expression pattern very similar to human embryonic stem cells (Invitrogen, Carlsbad, Calif.) (FIG. 7G). These data corroborate data presented herein that an increase in Oct-4 gene expression leads to an increase in Oct-4 protein expression. DNMT and HDAC11 have distinct functions with regard to regulation of transcription and chromatin remodeling. The inhibition of members from two separate regulatory groups resulted in a dramatic increase in the expression of Oct-4. Oct-4 protein expression was also increased in cells infected with DNMT1 and HDAC11 (FIG. 7E). Inhibition of DNMT1 and multiple HDACs resulted in increase in expression of Oct-4 protein.

There was no detectable increase in expression of Oct-4 in cells infected with HDAC7 and HDAC11 shRNA (FIG. 7F). This may be due a limitation of the experimental system. Alternatively, this result may suggest for optimal increase in expression of pluripotent genes, multiple pathways should be inhibited. Inhibiting the expression of genes that code for proteins that function in distinct regulatory complexes may result in higher expression levels of pluripotent genes. Any member of any regulatory complex may be inhibited.

Figure 8:
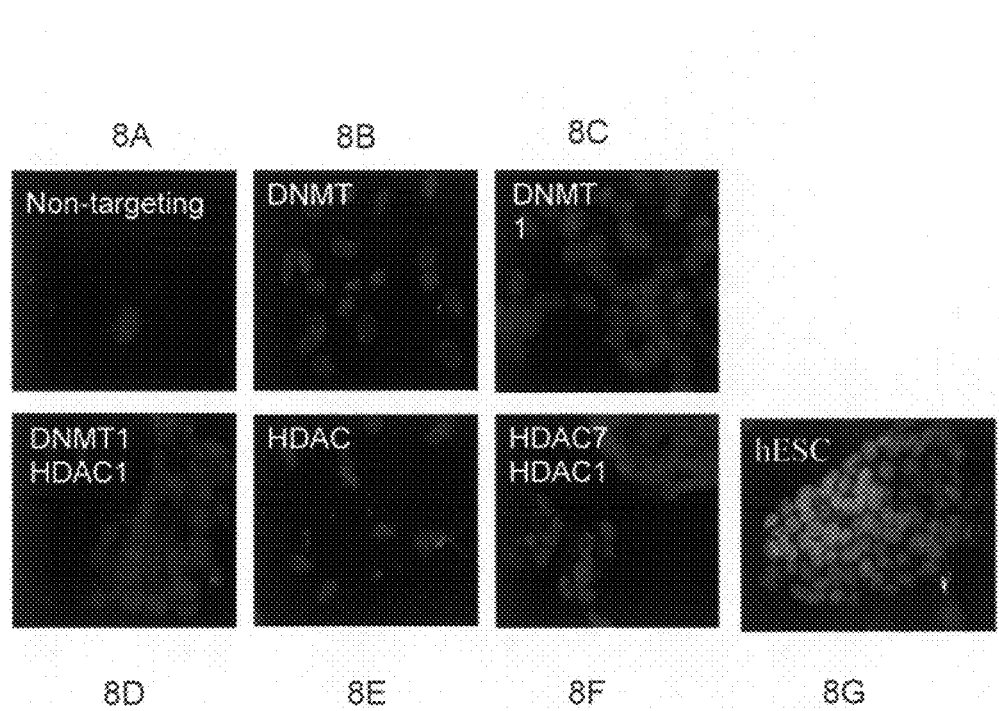
FIG. 8A is a photograph of fetal human dermal fibroblasts.
FIG. 8B is a photograph of fetal human dermal fibroblasts infected with DNMT1 shRNA.
FIG. 8C is a photograph of fetal human dermal fibroblasts infected with DNMT1 and HDAC7 shRNA.
FIG. 8D is a photograph of fetal human dermal fibroblasts infected with DNMT1 and HDAC11 shRNA.
FIG. 8E is a photograph of fetal human dermal fibroblasts infected with HDAC7 shRNA.
FIG. 8F is a photograph of fetal human dermal fibroblasts infected with HDAC11 and HDAC7 shRNA.
FIG. 8G is a photograph of human embryonic stem cells.

Sox-2 protein expression was increased in fetal human dermal fibroblasts (HDFf) by shRNA interference. FIG. 8A is a photograph of HDFf without infection (negative control) and FIG. 8G is a photograph of human embryonic stem cells (positive control). In the negative control cells, little expression of Sox-2 protein was detected. FIG. 8B is a photograph of HDFf cells infected with shRNA directed toward DNMT1. Nuclear staining was visible, however only a modest amount of Sox-2 protein was detected. HDFf cells infected with HDAC7 and DNMT1 shRNA showed minimal detection of Sox-2 protein (FIG. 8C). This may be due to the processing of this particular sample.

Cells infected with DNMT1 and HDAC11 shRNA showed a dramatic increase in the expression of Sox-2 protein (FIG. 8D). The inhibition of members from two separate regulatory groups resulted in a dramatic increase in the expression of Sox-2. Cells infected with HDAC7 shRNA showed minimal protein expression of Sox-2 (FIG. 8E). Sox-2 protein expression was also increased in cells infected with HDAC7 and HDAC11 (FIG. 8F). Inhibition of DNMT1 and multiple HDACs resulted in increase in expression of Sox-2 protein.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein.

What is claimed is:

1. A method for reprogramming a cell comprising: exposing a cell to an shRNA construct that interferes with expression of a gene that codes for a regulatory protein selected from the group consisting of histone deacetylase and DNA methyltransferase, wherein interfering with expression of said gene induces expression of a pluripotent gene selected from the group consisting of Oct-4, Nanog and Sox-2; and selecting a reprogrammed cell.

2. The method of claim 1, wherein said selecting said cell comprises: comparing phenotypes of the cell prior to and after exposure to said shRNA construct, and identifying a cell with a phenotype consistent with a reprogrammed cell.

3. The method of claim 1 further comprising: expanding the selected cell to a population of cells.

4. The method of claim 1, wherein said selecting a cell comprises: isolating a cell using an antibody directed to a protein coded for by a pluripotent gene or a cell-surface marker.

5. The method of claim 4, wherein said cell surface marker is selected from the group consisting of: SSEA3, SSEA4, Tra-1-60, and Tra-1-81.

6. The method of claim 1 further comprising: prior to selecting said cell, comparing chromatin structure of said pluripotent gene prior to exposure to said shRNA construct to the chromatin structure obtained after exposure to shRNA construct.

* * * * *